US010688251B2

(12) United States Patent
Davis et al.

(10) Patent No.: US 10,688,251 B2
(45) Date of Patent: Jun. 23, 2020

(54) SELF-RIGHTING TIP CAP

(71) Applicant: NEOMED, INC., Woodstock, GA (US)

(72) Inventors: Benjamin Martin Davis, Woodstock, GA (US); Aaron N. Ingram, Canton, GA (US); Mark M. Costello, County Mayo (IE)

(73) Assignee: NeoMed, Inc., Woodstock, GA (US)

(*) Notice: Subject to any disclaimer, the term of this patent is extended or adjusted under 35 U.S.C. 154(b) by 587 days.

(21) Appl. No.: 14/844,922

(22) Filed: Sep. 3, 2015

(65) Prior Publication Data

US 2016/0067422 A1 Mar. 10, 2016

Related U.S. Application Data

(60) Provisional application No. 62/047,364, filed on Sep. 8, 2014, provisional application No. 62/138,156, filed
(Continued)

(51) Int. Cl.
*A61M 5/32* (2006.01)
*A61M 5/31* (2006.01)

(52) U.S. Cl.
CPC ........ *A61M 5/3202* (2013.01); *A61M 5/3134* (2013.01); *A61M 2005/312* (2013.01); *A61M 2005/3104* (2013.01)

(58) Field of Classification Search
CPC ........ A61M 5/3202; A61M 2005/3104; A61M 2005/3117; A61M 2005/3118; A61M 2005/312; A61M 5/3134
See application file for complete search history.

(56) References Cited

U.S. PATENT DOCUMENTS 3,344,786 A 10/1967 Berg et al.
3,572,337 A 3/1971 Schunk
(Continued)

FOREIGN PATENT DOCUMENTS

EP 2269685 A2 1/2011
FR 2930428 A1 10/2009
(Continued)

OTHER PUBLICATIONS

Baxa Self-Righting Luer Tip Caps; www.iso-med.com; 1 pg; 2008.
(Continued)

*Primary Examiner* — Manuel A Mendez
*Assistant Examiner* — Tasnim Mehjabin Ahmed
(74) *Attorney, Agent, or Firm* — Dority & Manning, P.A.

(57) ABSTRACT

A self-righting tip cap includes a cap body having a generally oblate spheroid external shell geometry defining a first end and a second end. The first end has a base surface, and at least one clip extends from the body towards the second end. A coupling element accessible from the second end provides removable attachment of the tip cap to a cooperating coupling of a syringe or other female ENFit connectors. The geometry of the tip cap causes it to tend toward uprighting itself when dropped onto a flat surface, such that the base surface is in contact with the flat surface and the coupling element is accessible in an upward facing orientation. According to example forms, at least one rib of a female coupling can become interengaged with at least a portion of the clips such that the self-righting tip cap can be pulled and/or rotationally moved relative to the female coupling to be removed therefrom.

32 Claims, 20 Drawing Sheets

Related U.S. Application Data on Mar. 25, 2015, provisional application No. 62/174,289, filed on Jun. 11, 2015, provisional application No. 62/192,618, filed on Jul. 15, 2015.

(56) References Cited

U.S. PATENT DOCUMENTS

| | | | |
|---|---|---|---|
| 3,712,749 A | | 1/1973 | Roberts |
| 3,937,211 A | * | 2/1976 | Merten .......... A61B 5/150908 |
| | | | 600/578 |
| 4,043,334 A | * | 8/1977 | Brown ............... A61M 5/3134 |
| | | | 604/199 |
| 4,286,591 A | | 9/1981 | Raines |
| D309,710 S | | 8/1990 | Groves |
| D310,028 S | | 8/1990 | Brandt et al. |
| D378,233 S | | 2/1997 | Warner |
| 5,797,885 A | | 8/1998 | Rubin |
| D432,916 S | | 10/2000 | Drinkwater et al. |
| 6,270,519 B1 | | 8/2001 | Botts |
| 6,632,199 B1 | * | 10/2003 | Tucker ............... A61M 5/3134 |
| | | | 604/192 |
| 6,749,092 B2 | | 6/2004 | Olechowski et al. |
| D547,657 S | | 7/2007 | Tacchella |
| 7,316,669 B2 | * | 1/2008 | Ranalletta .......... A61M 5/3134 |
| | | | 604/199 |
| 7,367,964 B2 | * | 5/2008 | Heinz .................. A61M 5/347 |
| | | | 604/243 |
| D596,487 S | * | 7/2009 | Batton ................. A61M 5/347 |
| | | | D9/447 |
| D602,355 S | | 10/2009 | Waaland |
| D617,187 S | | 6/2010 | Murray |
| 8,016,795 B2 | | 9/2011 | Barrelle et al. |
| 8,099,932 B2 | | 1/2012 | Peacop et al. |
| 8,343,041 B2 | | 1/2013 | Byers et al. |
| D682,688 S | | 5/2013 | Murray |
| D684,055 S | | 6/2013 | Kwon |
| D684,057 S | * | 6/2013 | Kwon ........................... D9/453 |
| D686,495 S | | 7/2013 | Murray |
| 8,528,757 B2 | | 9/2013 | Bisio |
| D692,143 S | | 10/2013 | Shahidi Bonjar |
| D705,061 S | | 5/2014 | Jo et al. |
| D710,695 S | | 8/2014 | Pritikin |
| D712,744 S | | 9/2014 | Neputy et al. |
| D713,247 S | | 9/2014 | Webster et al. |
| D715,143 S | | 10/2014 | Hewitt et al. |
| D715,146 S | | 10/2014 | Holmes |
| D726,308 S | | 4/2015 | Shubin, Sr. et al. |
| 9,016,473 B2 | | 4/2015 | Tamarindo |
| D731,647 S | | 6/2015 | Nishioka et al. |
| D735,038 S | | 7/2015 | Tamarindo |
| D741,996 S | | 10/2015 | Strong et al. |
| D759,486 S | | 6/2016 | Ingram et al. |
| D796,326 S | | 9/2017 | Ichikawa et al. |
| 2004/0039341 A1 | * | 2/2004 | Ranalletta .......... A61M 5/3134 |
| | | | 604/199 |
| 2004/0116869 A1 | * | 6/2004 | Heinz .................. A61M 5/347 |
| | | | 604/181 |
| 2010/0252564 A1 | | 10/2010 | Martinez et al. |
| 2012/0109072 A1 | * | 5/2012 | Tabata .................. A61M 5/28 |
| | | | 604/192 |
| 2016/0067147 A1 | | 3/2016 | Davis et al. |
| 2016/0067422 A1 | | 3/2016 | Davis et al. |
| 2016/0317393 A1 | | 11/2016 | Davis et al. |

FOREIGN PATENT DOCUMENTS

| | | | |
|---|---|---|---|
| JP | H10297655 A | 11/1998 | |
| WO | 9200717 A1 | 1/1992 | |
| WO | 2008128074 A2 | 10/2008 | |
| WO | 2012024370 A1 | 2/2012 | |
| WO | 2014049097 A1 | 4/2014 | |
| WO | WO 2014160911 A1 * | 10/2014 | ............. A61M 5/31 |
| WO | 2016040126 A1 | 3/2016 | |
| WO | 2018022631 A1 | 2/2018 | |

OTHER PUBLICATIONS

Comar Tip Caps; 1 pg; date unknown.
Alternative Syringes Low Displacement Option PowerPoint Presention; Presented by Rork Swisher of Covidien; ISO 80369 Series Meeting; Berlin Germany; 11 pgs; Mar. 19, 2014.pgs.
International Search Report & Written Opinion for PCT/US2016/023771; dated Jun. 27, 2016; 17 pgs.
New ISO Tubing Connector Standards: A Follow-Up to the Sentinel Event Alert Webinar PowerPoint Presention; www.jointcommission.org; 50 pgs; Dec. 3, 2014.
New Tube Feeding Connectors Webinar PowerPoint Presention; www.oley.org; 24 pgs; Jun. 24, 2014.
International Search Report & Written Opinion for PCT/US2015/048380; 10 pgs; dated Oct. 29, 2015.
NeoMed Self-Righting Tip Cap; 1 pg; 2008.
Invitation to Pay Additional Fees for PCT/US2018/021856; dated Jun. 27, 2018; 24 pgs.

* cited by examiner

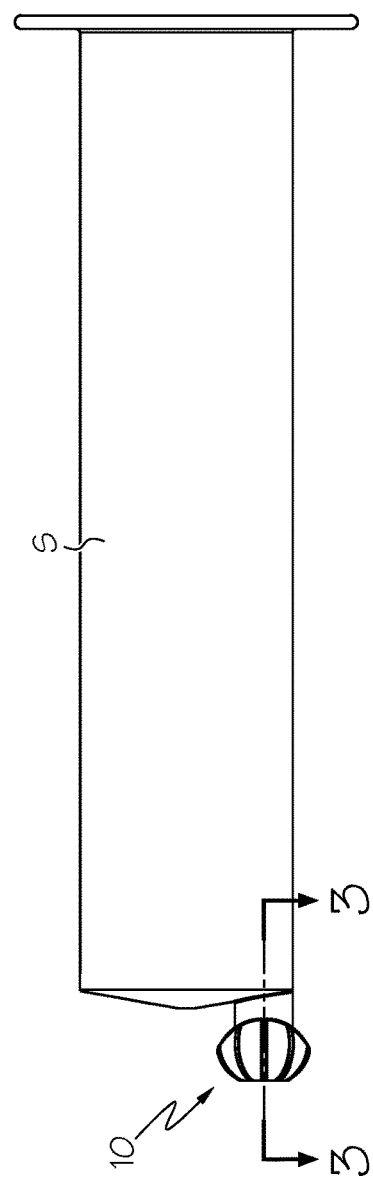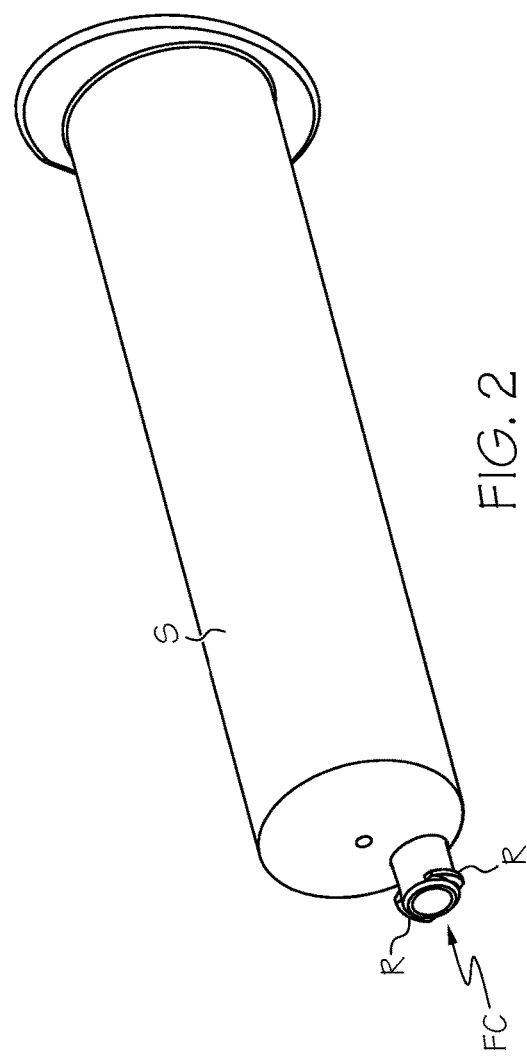

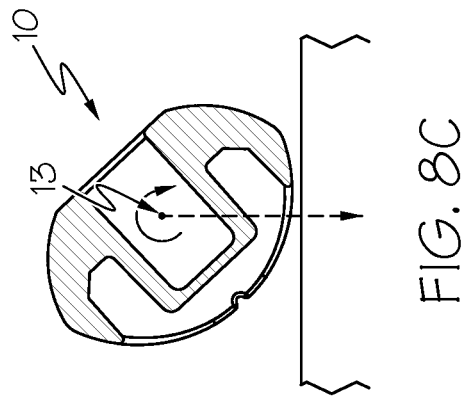
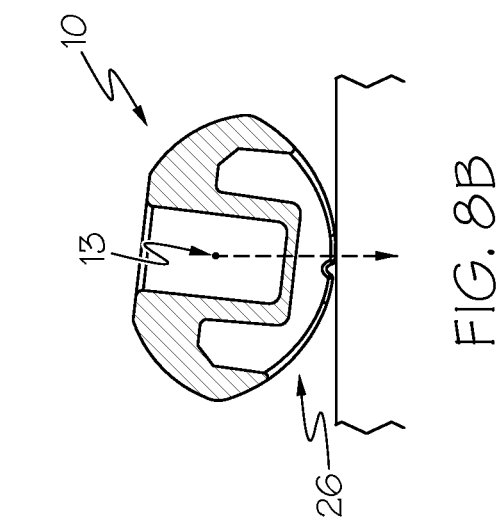
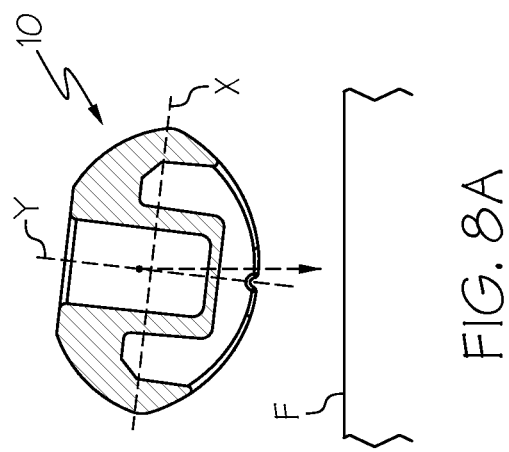
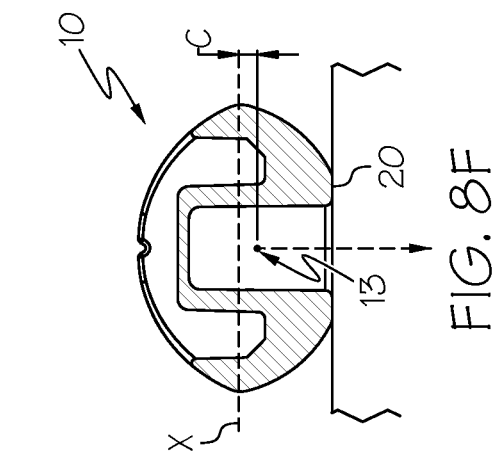
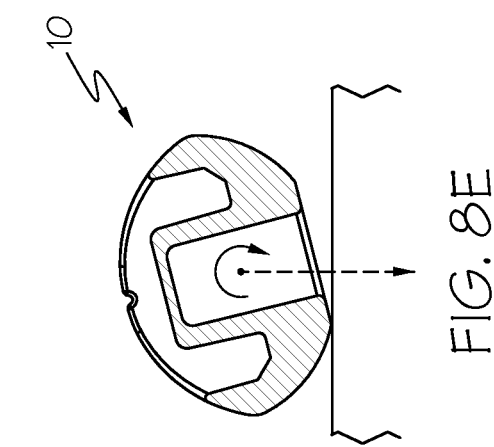
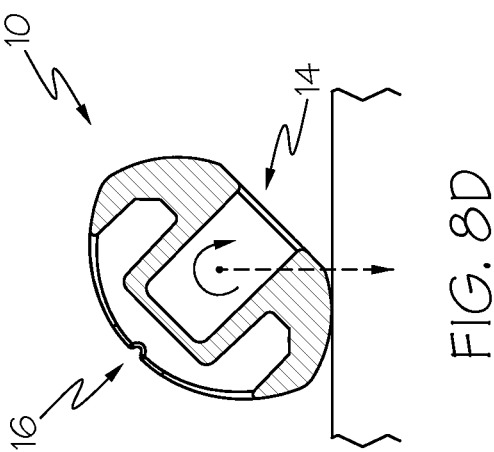

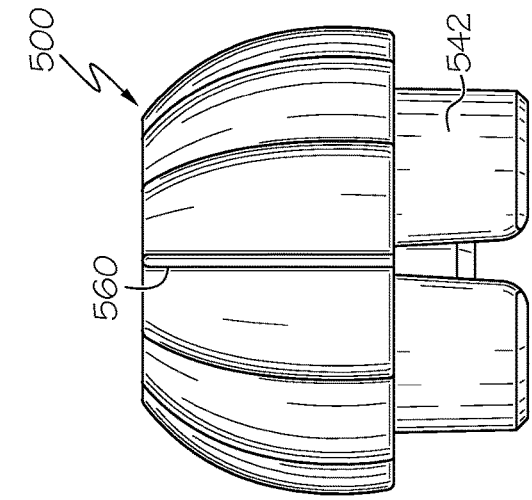
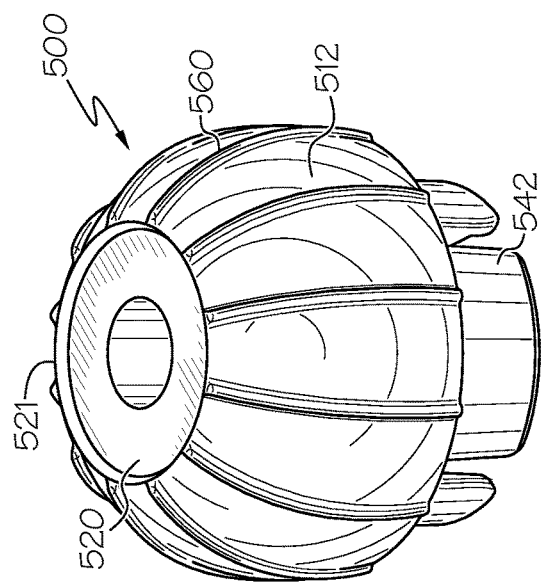
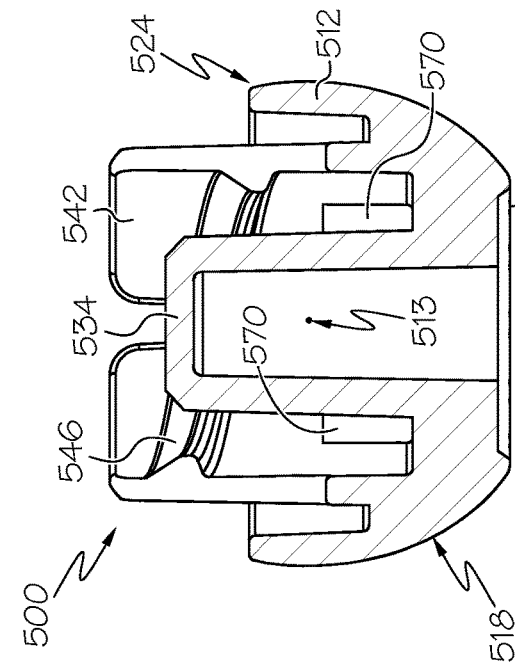
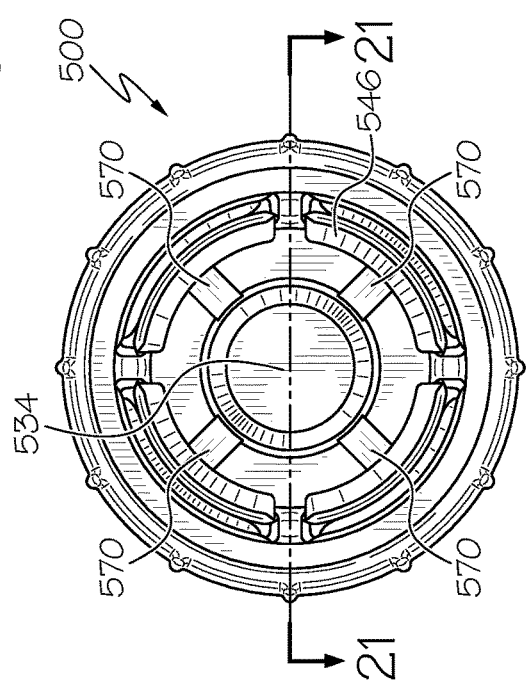

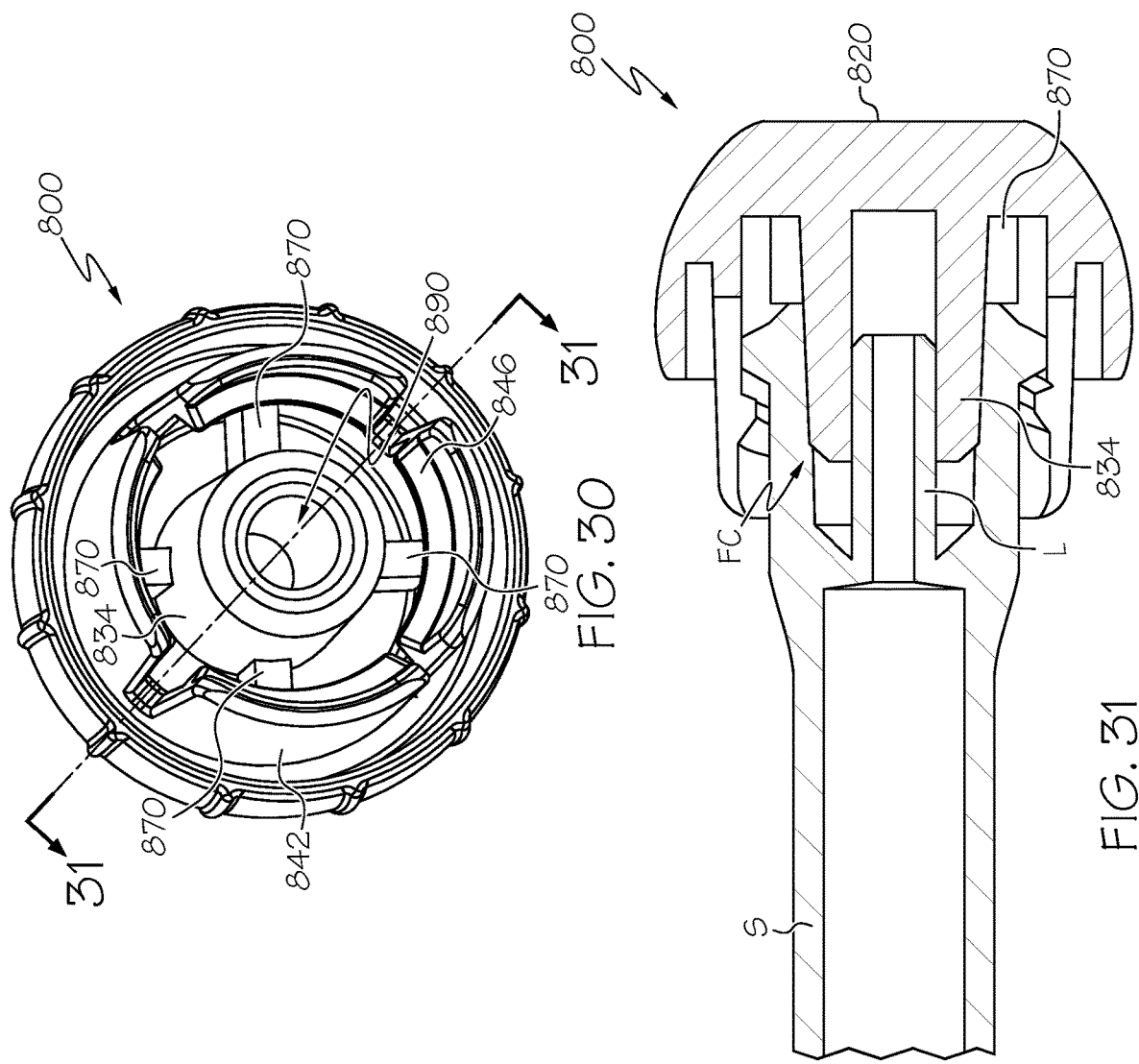

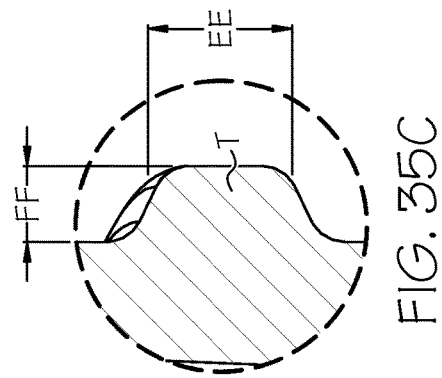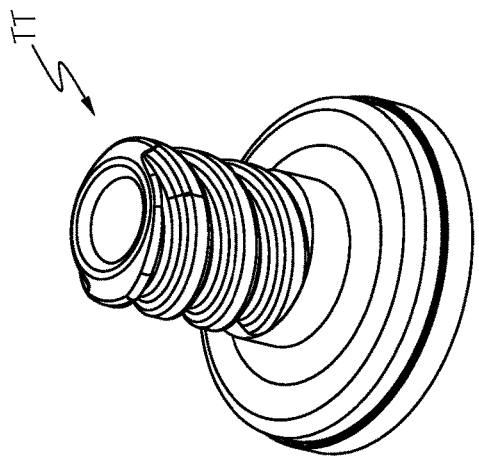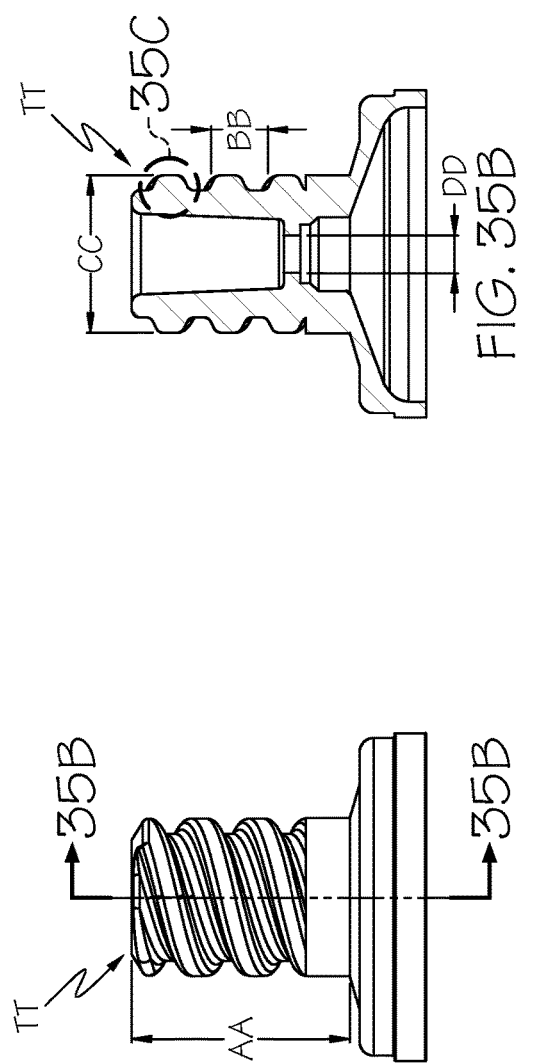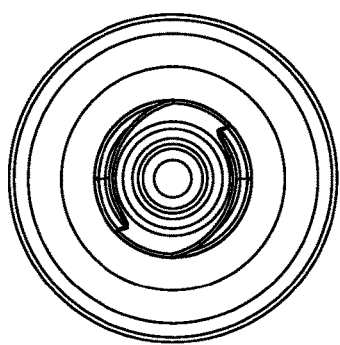
FIG. 35C
FIG. 35E
FIG. 35B
FIG. 35D
FIG. 35A

SELF-RIGHTING TIP CAP

CROSS-REFERENCE TO RELATED APPLICATIONS

This application claims the benefit of U.S. Provisional Patent Application Ser. No. 62/047,364 filed Sep. 8, 2014, U.S. Provisional Patent Application Ser. No. 62/138,156 filed Mar. 25, 2015, U.S. Provisional Patent Application Ser. No. 62/174,289 filed Jun. 11, 2015 and U.S. Provisional Patent Application Ser. No. 62/192,618 filed Jul. 15, 2015, the entireties of which are hereby incorporated herein by reference for all purposes.

TECHNICAL FIELD

The present invention relates generally to the field of medical devices, equipment and supplies, and more particularly to a self-righting cap for capping a syringe or the like.

BACKGROUND

Healthcare patients are commonly given fluids such as medication and nutrients by being connected to enteral fluid-delivery systems via fluid vessels. Common fluid vessels for delivering such fluids include small-bore tubes and catheters. A problem arises when these fluid tubes are misconnected. That is, when a tube from one fluid delivery system is connected to a tube intended for connection to another fluid delivery system that serves a completely different function, for example, when a feeding administration set is inadvertently connected to a tracheostomy tube. Such tubing misconnections are also referred to as LUER misconnections, small-bore misconnections, or wrong-route errors. Tubing misconnections have resulted in patient injury and deaths, and are widely recognized as underreported.

An underlying cause of these misconnections has been attributed to the universal design of LUER connectors, which are one of the most commonly used types of small-bore connectors in healthcare. These connectors used to connect the tubing of one medical device to another. However, the simple design and ease of use of LUER connectors allows the tube of the device for one delivery system to be connected to tube of an unrelated system that has a different intended use (e.g., vascular, enteral, respiratory, epidural, or intrathecal), resulting in healthcare providers inadvertently connecting wrong systems together and thereby causing liquids (e.g., medications or enteral feedings) or gases (e.g., oxygen) to be delivered through the wrong route.

Efforts are underway to develop standards, such as the ISO 80369 standards, for tubing connections. These standards hold the promise of significantly addressing the tubing misconnection problem. For example, these standards provide for a new connector for enteral feeding tubes that prevents misconnection to non-enteral connectors. This new connector is also referred to as the ENFit connector.

In addition to the ENFit connector being implemented on enteral feeding tubes, the syringes that contain and deliver the fluids (nutrients or medicine) will generally also have the ENFit connector to provide for connection with the tubes. In many cases, a plurality of syringes are filled and capped or sealed in batches. Commonly, the cap or protector that is used to temporarily seal a syringe is small in size and is designed to be coupled to the connector of the syringe in a particular orientation. Some caps have been developed to "self-right" or orientate a particular way (i.e., with their coupling feature face up) when dropped onto a surface, such that connecting the cap with the syringe is relatively easy and quick. But known self-righting caps are not compatible with the ENFit connector standards.

Continued improvements to self-righting caps or protectors is sought. It is to the provision of a self-righting tip cap meeting these and other needs that the present invention is primarily directed.

SUMMARY

In example embodiments, the present invention provides a self-righting tip cap for temporarily sealing a syringe or other connector. In one aspect, the present invention relates to a self-righting tip cap including a body having a generally oblate spheroid external geometry with a first end and a second end at opposite sides of the cap body. A base surface is provided at the first end and defines a generally planar rim surrounding the base surface. At least one clip extends from the cap body towards the second end. In example forms, an interior face of the clip includes an indent protruding therefrom. Optionally, a coupling element is accessible from the second end of the cap body. Generally, the coupling element provides for removable engagement with a connector of the syringe.

In example embodiments, the at least one clip provides for removable coupling to a portion of the connector. In some example forms, the indent protruding from the at least one clip is in the form of a thread. In some example forms, the at least one clip is generally resiliently flexible. An annular recess generally surrounds the coupling element. According to example forms, at least one opening is formed within the base surface and communicates with the annular recess. Optionally, at least one rib or support is positioned within the annular recess and extends between an interior portion of the at least one clip and the coupling element. Optionally, grooves or indents may extend along an outer surface of the cap body. Optionally, the coupling element includes an orifice formed therein for receiving a lumen extension tip of a connector of a syringe.

In another aspect, the invention relates to a syringe and tip cap assembly. In example forms, the syringe and tip cap assembly generally includes a syringe having a connector and a self-righting tip cap. The self-righting tip cap is generally configured for removable attachment to the connector of the syringe. In example forms, the self-righting tip cap includes a cap body, a base surface, and at least one clip. The cap body includes a generally oblate spheroid external geometry with a first end and a second end at opposite sides of the cap body. The base surface is provided at the first end and defines a generally planar rim surrounding the base surface. And, the at least one clip extends from the cap body towards the second end.

In yet another aspect, the present invention relates to a self-righting tip cap including a cap body having a generally oblate spheroid external geometry with a first end and a second end at opposite sides of the cap body. A base surface at the first end defines a generally planar contact surface. An irregular surface is provided at the second end. Preferably, a coupling element is provided and is accessible from the second end, and wherein the coupling element does not extend beyond the second end. at least one clip extends from the cap body towards the second end, and wherein an interior face of the at least one clip comprises an indent protruding therefrom.

In example forms, the irregular surface includes alternating peaks and valleys at the second end. A coupling extends from the first end towards the second end, and an annular channel surrounds the coupling. In example forms, the alternating peaks and valleys include a wave-like profile. The wave-like profile has smooth and radiused transitions between the peaks and the valleys. The coupling generally extends beyond the valleys but does not extend beyond the peaks. In example forms, the coupling provides for removable engagement with a connector of a syringe, for example a syringe having an ENFit or ISO 80369 compatible connector. Optionally, at least one groove is formed on an outer surface of the bulbous body.

In still another aspect, the present invention relates to a syringe and tip cap assembly including a syringe and a self-righting tip cap. The syringe includes a threaded tip having a substantially continuous external threads extending along at least a portion thereof. The self-righting tip cap configured for removable attachment to the threaded tip of the syringe. The self-righting tip cap includes a cap body, a base surface, and at least one coupling element. The cap body includes a generally oblate spheroid external geometry with a first end and a second end at opposite sides of the cap body. The base surface is provided at the first end and defines a generally planar contact surface. The at least one coupling element is compatible with the substantially continuous external threads of the threaded tip of the syringe.

In example forms, the at least one coupling element of the tip cap is positioned at the second end of the cap body, which is generally opposite the base surface. The at least one coupling element includes a generally central coupling and an annular recess formed around the coupling. An outer wall of the annular recess includes threads protruding therefrom for removable engagement with the threaded tip of the syringe. Optionally, a lumen extension tip is formed within the threaded tip of the syringe and the coupling includes an orifice for receiving the lumen extension tip.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 1 is a side view of a self-righting tip cap coupled to a syringe, according to an example embodiment of the present invention.

FIG. 2 is a perspective view of the syringe of FIG. 1, with the self-righting tip cap removed.

FIGS. 8A-F show cross sectional views of the self-righting tip cap of FIG. 8 taken along line 8-8, and showing a sequence of the self-righting tip cap being released onto a flat surface and self-righting itself.

FIGS. 18-21 show several views of a self-righting tip cap according to another example embodiment of the present invention.

FIG. 30 shows a rear end perspective view of a self-righting tip cap according to another example embodiment of the present invention.

FIG. 31 shows a cross-sectional view of the self-righting tip cap of FIG. 30 removably coupled to a female connector of a syringe, whereby a coupling of the tip cap is configured to receive a lumen of the female coupling.

FIG. 35A-E shows a dimensioned threaded syringe tip for receiving the self-righting tip cap of FIGS. 32-34.

DETAILED DESCRIPTION OF EXAMPLE EMBODIMENTS

Figure 3:
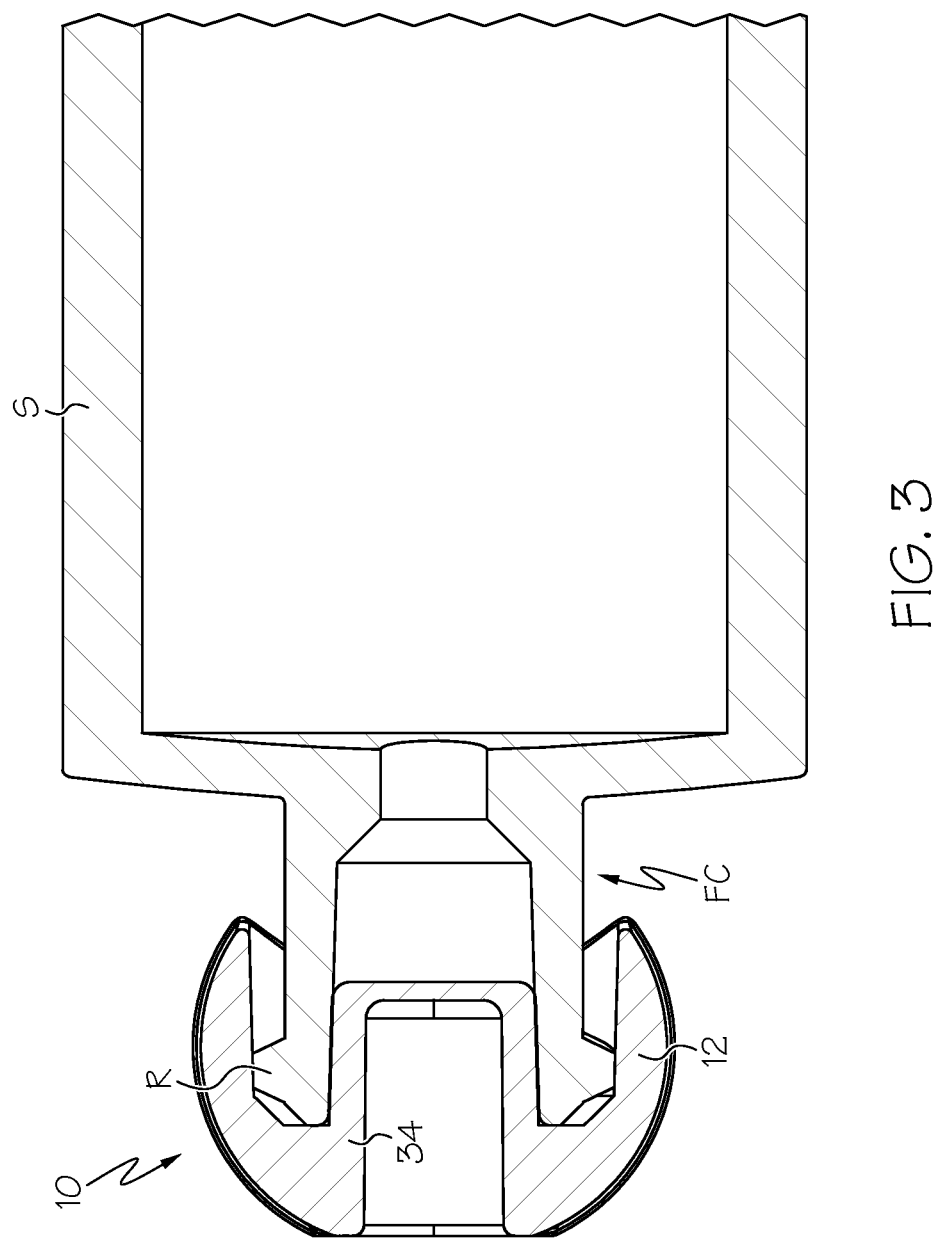
FIG. 3 is a cross sectional view of the self-righting tip cap coupled to the syringe of FIG. 1 taken along line 3-3.
Figure 4:
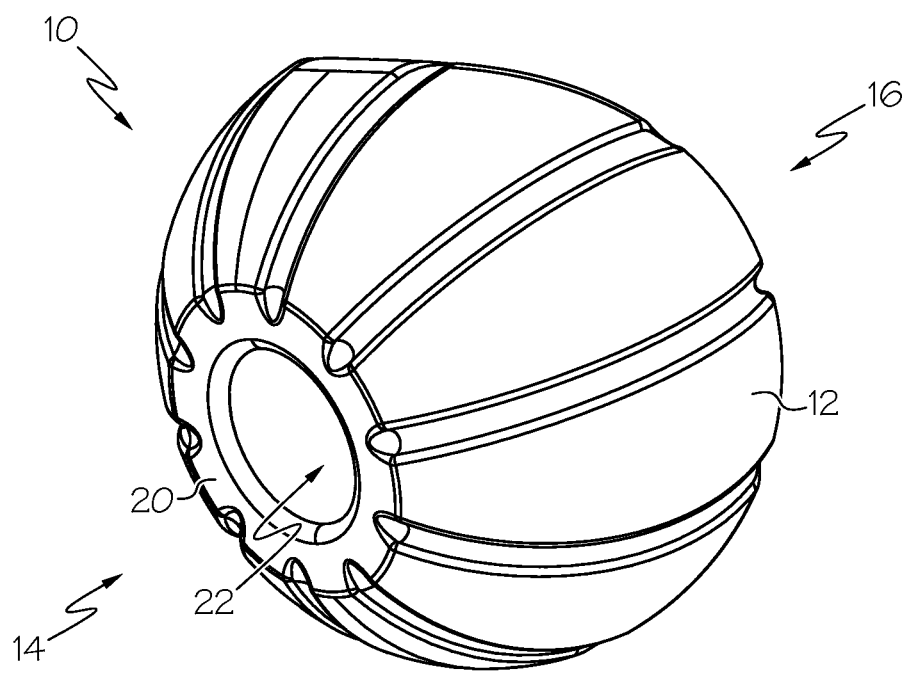
FIG. 4 is a detailed front perspective view of the tip cap shown in FIG. 1, removed from the syringe.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIG. 1 shows a self-righting tip cap 10 mounted to a female coupling or connector FC of a syringe S according to an example embodiment and manner of use of the present invention. The syringe S may be for example a storage and transfer syringe for transferring breast milk from a breast pump collection container to a feeding bottle, or for preparing formula, supplements, medication, or other enteral fluids for feeding a neonate. In alternate embodiments, the tip cap 10 can be used to temporarily close various other types of containers, fluid conduits and tubing, and/or other equipment having a compatible coupling thereon.

As shown, the tip cap 10 is removably coupled to the female connector FC such that a fluid, nutrients, or other liquids can be transferred to and from the syringe S when the tip cap 10 is removed from the syringe coupling, and wherein the tip cap prevents contamination from entering the syringe and prevents leakage from the syringe when installed. In many institutional applications (e.g., hospitals and neonatal care centers) a plurality of syringes S are filled for use, and each individual syringe is capped or sealed. To cap the syringes quickly and efficiently, it is a common practice for care providers or technicians to "spike" the female connector FC of the syringe onto a tip cap 10. To do so, the tip cap 10 should be oriented correctly (i.e., with its coupling side up) to allow coupling between the female connector FC of the syringe S and a male adaptor or coupling 34 of the tip cap 10 without having to manipulate the tip cap into the proper orientation for attachment onto the syringe.

In an example form, the female connector FC of the syringe S is in the form of an ENFit female connector according to the global design standard ISO 80369-1 (see FIG. 2). Generally, the female connector FC comprises a pair of thread lugs or ribs R extending along a portion of the periphery of the connector. As will be described below, the tip cap 10 preferably provides for removable engagement with the female connector FC of the syringe S without generally interfering with the ribs R thereof. Optionally, the tip cap can be provided to seal with or prevent contamination with other couplings or connectors, luers, feeding tubes, other tubes, etc.

FIGS. 4-7 show the self-righting tip cap 10 in greater detail. In example forms, the tip cap 10 comprises a bulbous shell or body 12 having a first end 14 and a second end 16. The cap body 12 generally comprises an oblate spheroid external geometry that is somewhat flattened at the ends 14, 16 of its minor axis Y (see FIG. 7), although other shell geometries may be utilized. Preferably, the body 12 is shaped and weighted such that the tip cap 10 will tend to right itself and come to equilibrium in a particular orientation (i.e., coupling side up) when coming into contact with a support surface under the influence of gravity (as will be described below), at least in a majority of instances and preferably in a substantial majority or substantially all instances. The first end 14 comprises a generally planar rim around a base surface 20 that generally surrounds an orifice 22, and the second end 16 comprises an undulating or irregular profile 24 comprising opposing pairs of peaks 26 and valleys 30.

Figure 5:
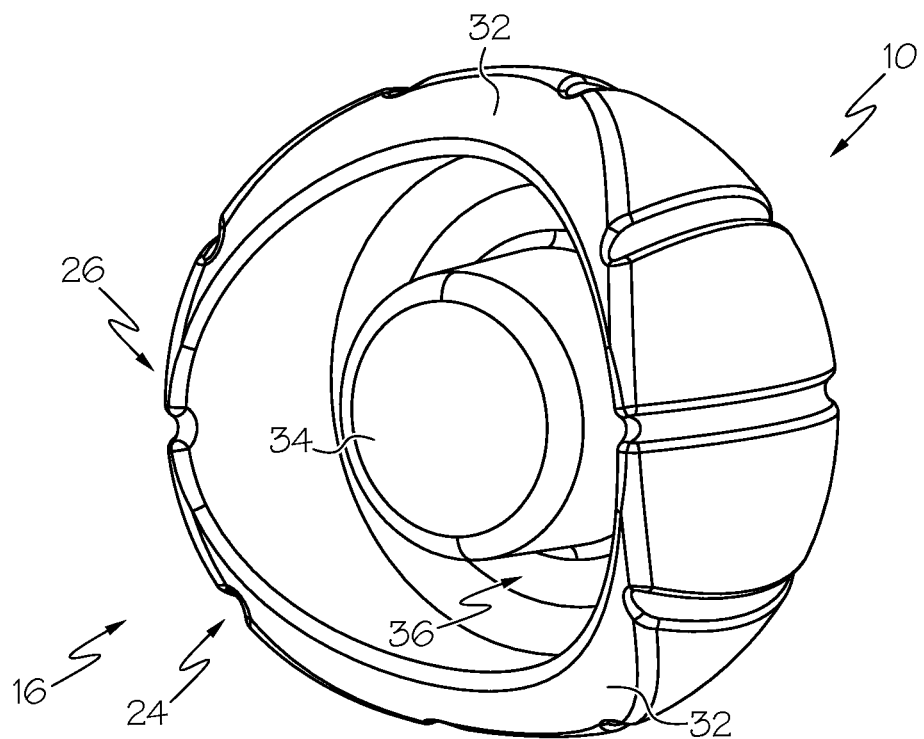
FIG. 5 is a rear perspective view of the tip cap of FIG. 4.
Figure 6:
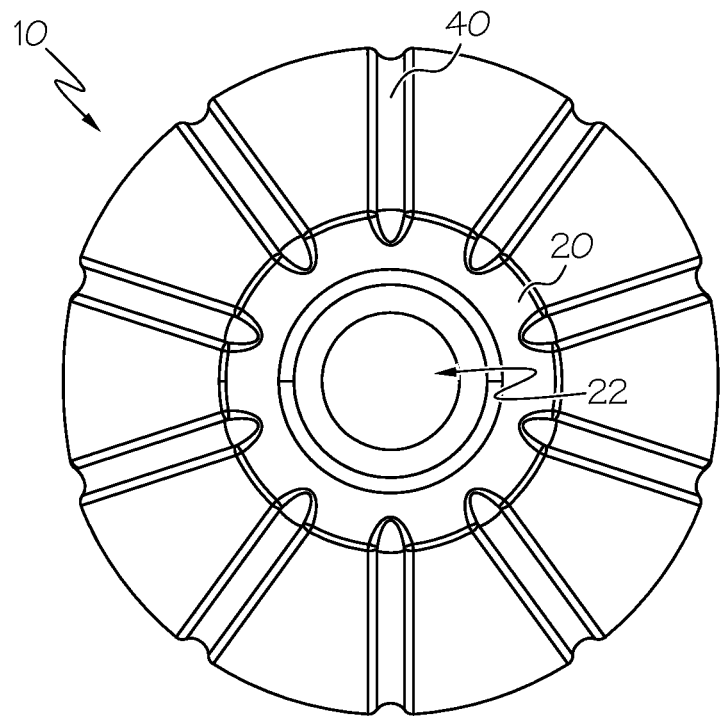
FIG. 6 is a top external view of the self-righting tip cap of FIG. 4.
Figure 7:
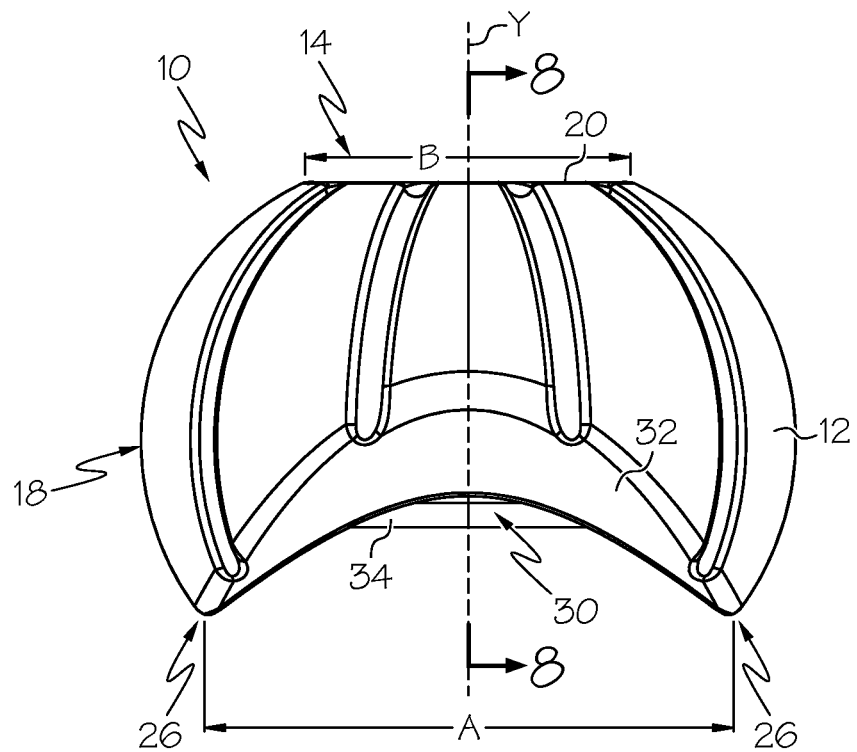
FIG. 7 is a side view of the self-righting tip cap of FIG. 4.

The base surface 20 is generally flat to provide for stable resting against a support surface, for example, a table, desk, counter, etc. Preferably, as described below, the tip cap 10 will right itself and become stable or rest in an orientation where the base surface 20 is in contact with the flat surface. Conversely, the undulating profile 24 of peaks 26 and valleys 30 is preferably configured to provide a generally non-planar or unstable surface, such that the tip cap 10 tends not to settle in equilibrium in an upside-down orientation. In one example form, the peaks 26 and valleys 30 define a wave-like profile, whereby the transition between the peaks 26 and valleys 30 is generally smooth and radiused. In alternate forms, the peaks and valleys may comprise more angular teeth or other irregular surface contours. In example embodiments, a smooth and radiused profile 24 (between the peaks and valleys and therewith) has been found to cause the tip cap 10 to generally remain unstable when contacting a support surface under the influence of gravity, and tending to roll or bounce toward the upright orientation (e.g., to a position where the base surface 20 is resting against the support surface and the coupling face 16 faces upwardly away from the support surface). Optionally, at least the peaks 26 comprise the radiused profile or another generally similar profile which will cause the tip cap 10 to be unstable when dropped from a height onto the support surface. Furthermore, the generally oblate spheroid external geometry or bulbous-shaped cap body 12 generally defines a curved side wall 18 (see FIG. 7), which generally extends continuously between the base surface 20 and the peaks 26. According to one example form, the curved side wall 18 comprises a substantially uniform radius between the base surface 20 and the peaks 26. Optionally, one or more at least partially different radii may be provided for varying the continuous curved side wall 18 as desired. In example embodiments, the external body contour of the tip cap 10 further comprises a flat or generally arcuate transition portion 32 adjacent the valleys 30. The flat 32 extends between each of the valleys 30 to a portion of the convex outer surface of the cap body 12. In example forms, when the peaks 26 of the tip cap 10 impact with the flat surface, their irregular shape imparts a rolling or tumbling motion on the tip cap. As the tip cap 10 begins to roll in either direction towards the upright orientation (e.g., with the base surface 20 being in contact with the flat surface), the flats 32 preferably provide a smooth transition and allows continuous movement or rolling of the tip cap, such that the outer surface of the bulbous cap body 12 contacts the flat surface and continues to roll until coming into the upright orientation, with its coupling 34 facing upward away from the support surface. According to example forms, As shown in FIG. 5, the male adapter or coupling 34 generally extends from the first end 14 towards the second end 16, inside of the shell of the cap body 12. In example forms, the orifice 22 in the first end 14 of the cap body 12 generally corresponds to the shape of the coupling 34, for example, generally cylindrical as depicted. Typically, the male coupling element 34 extends slightly beyond the valleys 30 in height (best seen with reference to FIG. 7), but preferably does not extend to or beyond the peaks 26, for example so that the coupling 34 does not interfere with the tip cap rolling away from contact of the second end 16 with the support surface and toward the upright orientation. An annular recess 36 is provided around the coupling 34 to provide clearance for the female coupling FC of the syringe S and the ribs R formed thereon. In one example form, the male coupling 34 will comprise a slight amount of draft or taper to provide frictional engagement within the female coupling FC of the syringe S and a substantially leak-proof seal when the male coupling 34 is inserted within the female coupling FC (see FIG. 3). The distal end of the male coupling preferably extends into the female coupling FC when the cap 10 is installed onto a syringe S, to reduce the amount of dead space in the syringe tip. Optionally, the male coupling 34 may be otherwise shaped to provide a sealing and releasable fit with a cooperative internal contour of the female connector FC of the syringe S. In alternate embodiments, for example, the cap 10 can be configured for a threaded screw-on connection with the syringe, a snap fit connection, or other means of removable attachment to the syringe. The cap body 12 of the tip cap 10 optionally comprises one or more channels or indentions 40 extending from the first end 14, along the outer surface of the bulbous body 12, and to the second end 16. Preferably, the channels 40 provide roughness or irregularity to the surface of the bulbous body 12 such that a user or physician can easily grasp/twist the tip cap 10 for installation and/or removal from the syringe S, and to resist rolling about the minor axis of the tip cap and bring the tip cap to rest when dropped onto a support surface. As depicted in FIG. 7, the peaks 26 generally define a width A therebetween and the base surface 20 generally defines a width B. According to example forms, the width A is generally greater than the width B, more preferably the width A is between about 1.25-1.5 times greater than the width B.

FIGS. 8A-F show a sequence of motion of the self-righting tip cap 10 according to an example method of use according to the present invention. As depicted in FIG. 8A, the tip cap 10 is generally dropped from an elevation above the support surface, and falls downwardly under the influence of gravity towards the flat surface F. If the tip cap falls in an upside down orientation (e.g., peaks 26 facing down) as shown, contact with the flat surface F (see FIG. 8B) causes the tip cap 10 to bounce and/or roll (see FIG. 8C). As shown in FIG. 8C, the center of mass 13 of the tip cap 10 is preferably located closer to the base surface 20 than to the contact face defined by the peaks 26 of the second end 16, which causes the rolling cap to tend toward the upright position (clockwise direction in the view of FIG. 8C). In example embodiments, the center of mass 13 of the tip cap 10 is located between the first end 14 and a plane defined by the major axis X of the oblate spheroid geometry of the cap body 12, further tending to upright the tip cap (see FIG. 8A). For example, as depicted in FIG. 8F, the center of mass 13 is spaced at a distance C from the plane defined by the major axis X. Optionally, the center of mass 13 may be positioned as desired, for example, which is generally placed between the plane defined by the major axis X and the first end 14 defined by the base surface 20. As shown in FIGS. 8D-E, the momentum of the initial rolling motion causes further rotation of the tip cap towards the upright orientation, which will eventually become stable and at rest in the upright configuration (see FIG. 8F).

In example embodiments, the self-righting tip cap 10 can be formed by an injection molding process. Preferably, the tip cap 10 is formed from a plastic material, for example, polypropylene thermoplastic. Optionally, other plastics, composites, rubbers, synthetic materials, natural materials, or other materials can be used as desired. In example embodiments, the material(s) of construction provide a coefficient of restitution sufficient to allow the cap to bounce from its upside-down orientation and settle in the upright orientation when dropped onto a hard surface. According to some example forms, the self-righting tip cap may be formed from two or more materials using a co-molding process (or other injection or molding processes).

FIGS. 9-13 show a tip cap 100 according to another example embodiment of the present invention. As depicted, the tip cap 100 is generally similar to the tip cap 10 as described above. In example forms, the tip cap 100 generally comprises a bulbous shell or body 112 having a first end 114 and a second end 116. The cap body 112 generally comprises an oblate spheroid external geometry that is somewhat flattened at the ends 114, 116 of its minor axis or elongate axis Y2, although other shell geometries may be utilized. Preferably, the body 112 is formed such that the tip cap 100 will tend to right itself and come to equilibrium in a particular orientation (i.e., coupling side up) when coming into contact with a support surface under the influence of gravity, at least in a majority of instances and preferably in a substantial majority or substantially all instances. The first end 114 comprises a generally planar rim or generally conical raised edge 121 around a base surface 120 that generally surrounds an orifice 122, and the second end 116 comprises a collar or circular array of couplings 140, which generally extend from the cap body 112. In example forms, a rim 124 is provided near an end of the body 112 near the second end 116. Typically, the rim 124 is substantially radiused to further assist the cap 100 in righting itself so that the planar rim or generally conical raised edge 121 is resting against the surface F (also see FIG. 13). According to some example forms, the rim 124 generally provides a smooth transition between the outer surface of the body 112 and the edge of the extension thereof extending towards the second direction 116. According to some example forms, the base surface 120 is recessed within the body 112 whereby the planar rim or generally conical raised edge 121 becomes in contact with the surface F such that the tip cap 100 is positioned in a coupling-side-up orientation, for example, whereby the coupling 134 is generally extending in a direction generally opposite the surface F and whereby the base surface 120 is generally laterally offset from the surface F (see FIG. 12). Optionally, the raised edge 121 can be shaped as desired, for example with a chamfered edge or other radiused edges other or transitional features as desired. According to some example forms, one or more cutouts may be formed in portions of the edge 121 for example, such that the area of the contact surface of the edge 121 in contact with the surface F is reduced. Optionally, one or more additional ring-like intents may be formed on the base surface 120 (and around the orifice to increase the surface area in contact with the surface F.

In example forms, four tab members or clips 142 generally form the circular array at a distance from the coupling 134 generally extending centrally from the body 112, which generally forms a portion of the orifice 122. Typically, each clip 142 comprises a chamfered, angled, radiused or end portion 144 near an outer edge thereof, and an internal portion or wall of at least one of the clips 142 preferably comprises a thread or thread-like ridge 146 generally protruding therefrom. In the depicted embodiment, each of the four clips 142 comprises at least a portion of a thread 146. In example forms, the tip cap 100 can be installed and removed either by pushing and pulling (without twisting) due to the snap connection provided by the split collar, or by twisting on and off due to the thread 146 on the clips 142, thus providing a dual-action installation and removal mechanism.

Figure 11:
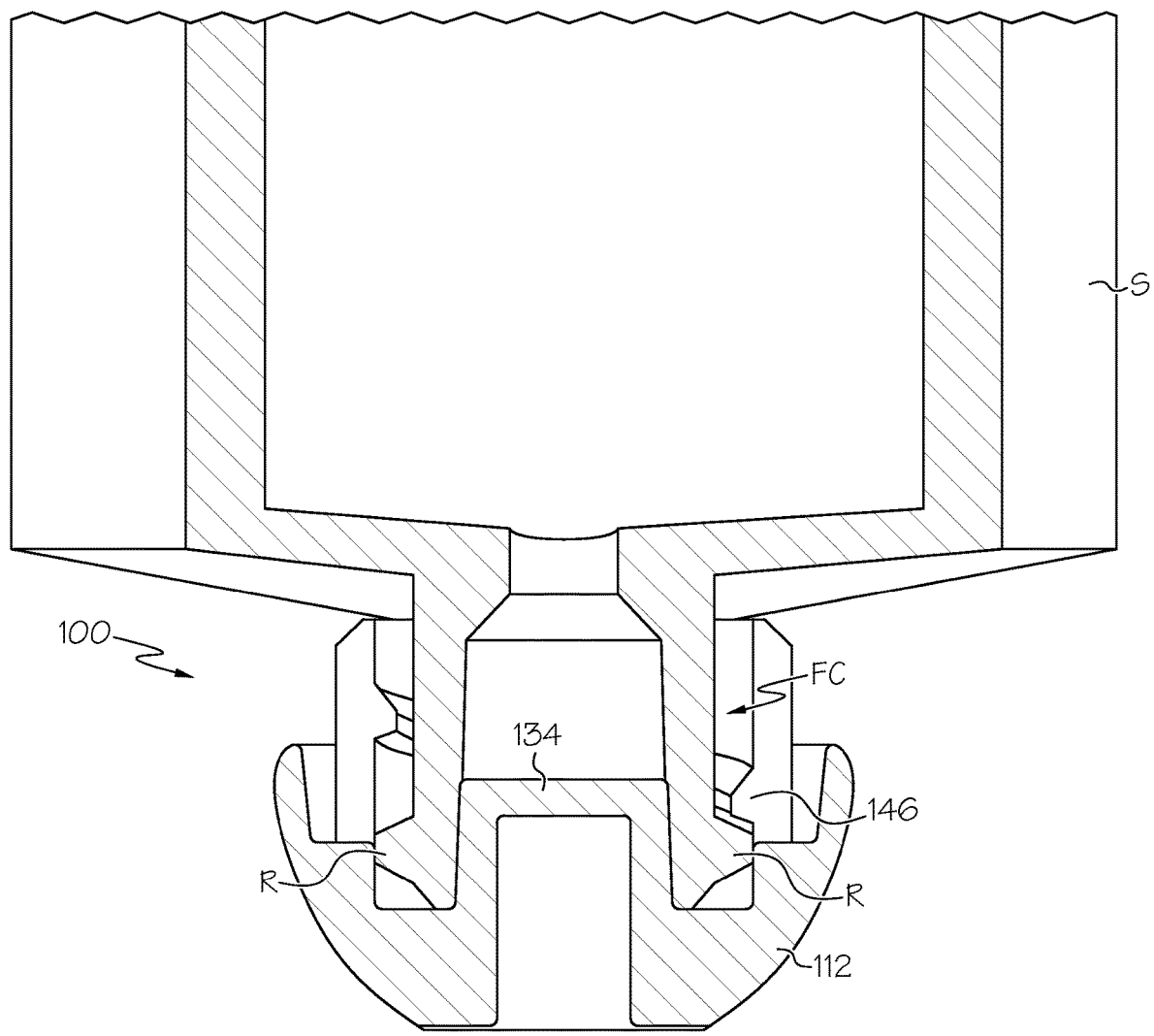
FIG. 11 shows a cross-sectional view of the self-righting tip cap of FIG. 10 coupled to the syringe.

Preferably, with the edge 121 resting against a flat surface F, the female coupling FC of the syringe S can be pressed against the second end 116 thereof to provide interengagement therebetween (see FIG. 11). Preferably, the ribs R eventually interengage with the threads 146 of the clips 142, which causes the clips 142 to generally flex outwardly, thereby permitting the ribs R to pass by. Preferably, the clips 142 are substantially resilient and flexible such that interengagement of the ribs R with the threads 146 allows for flexture of the clips 142. Conversely, when the female coupling FC is at least partially seated within an annular recess 136 defined between the coupling 134 and the clips 142, the ribs R become at least partially engaged with at least a portion of one of the threads 146 of the clips 142, and thus, the tip cap 100 is prevented from being easily pulled away from the female coupling FC. However, the tip cap 100 can be removed from the female coupling FC by rotation thereof relative to the female coupling FC whereby the ribs R are guided along the threads 146, for example, similar to the rotational threading engagement of a nut and bolt. In some example forms, inserting the female coupling FC within the cap 100 preferably causes the rotation of the cap as the coupling FC is inserted therein, for example, wherein the ribs R of the female coupling FC move along the threads 146 and wherein the clips 142 are substantially rigid such that interengagement of the ribs R with the threads 146 provides rotation thereto rather than outwardly flexture of the clips 142. In most example forms, the clips 142 and/or threads 146 of the cap comprise a lead-in or angle or taper, which allows for a friction/interference fit.

Figure 9:
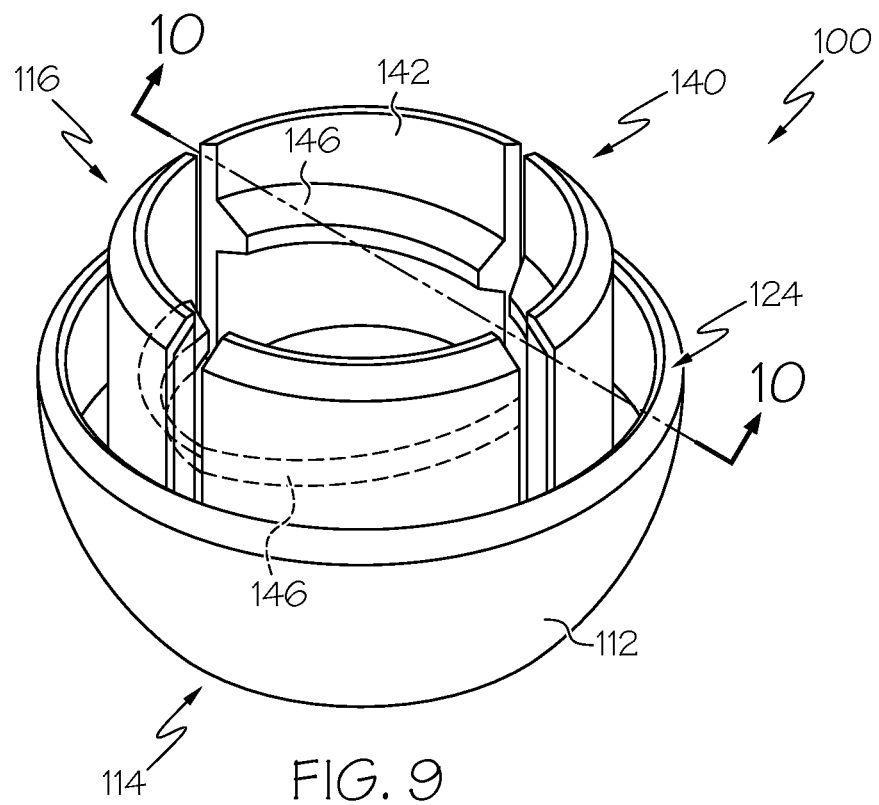
FIG. 9 shows a perspective view of a self-righting tip cap according to another example embodiment of the present invention.
Figure 10:
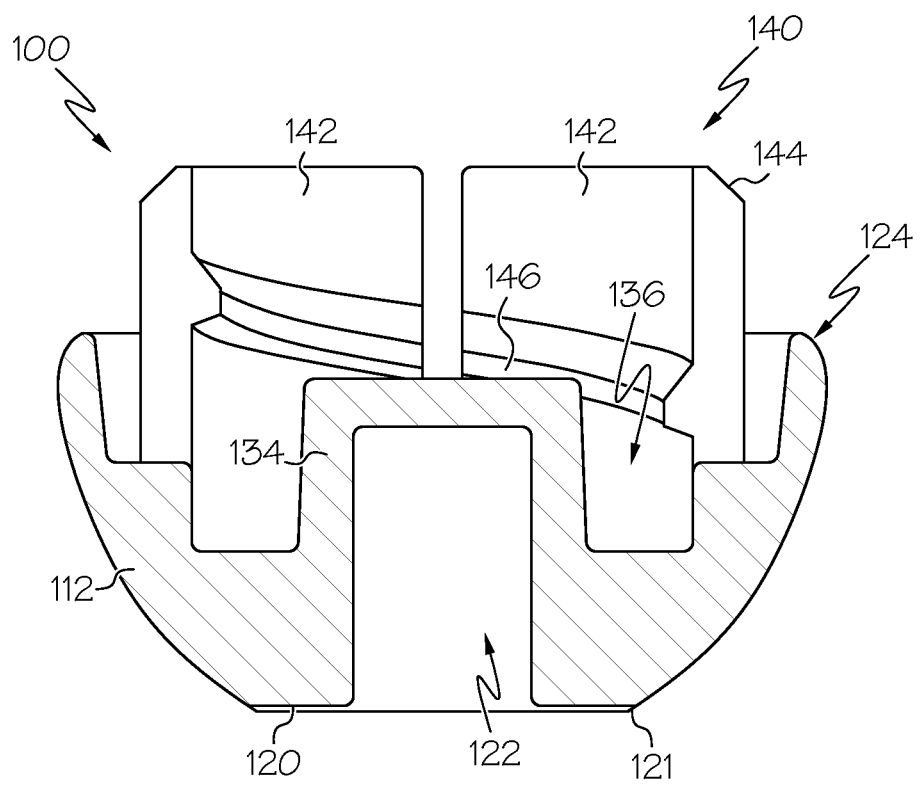
FIG. 10 shows a cross-sectional view of the self-righting tip cap of FIG. 9 taken along line 10-10.
Figure 12A:
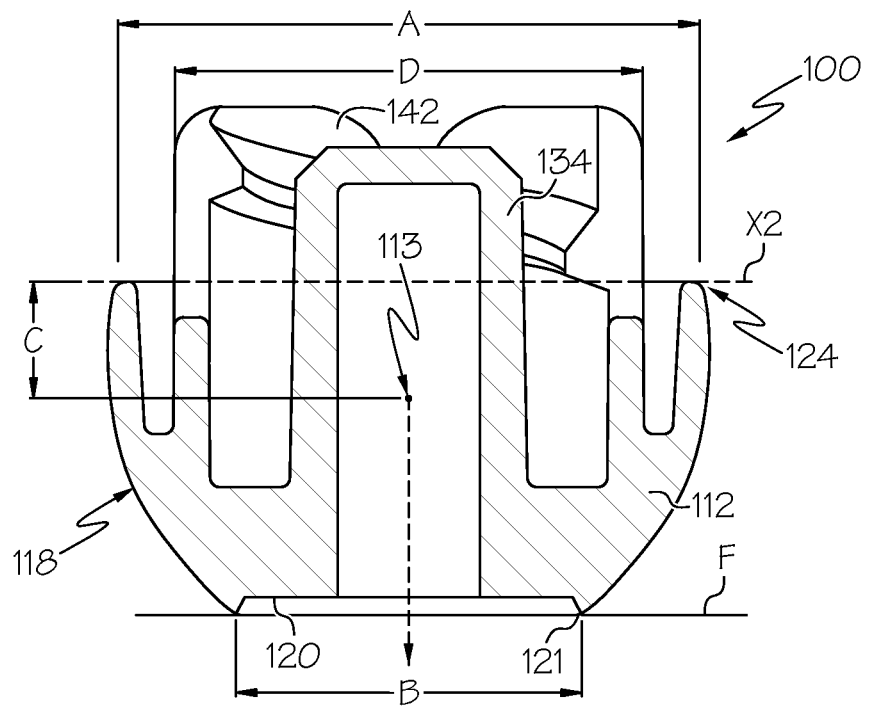
FIGS. 12A-B show cross-sectional views of the self-righting tip cap of FIG. 10 in different orientations, and indicating the location of the center of gravity thereof, and showing the coupling portion thereof sized according to another example embodiment of the present invention.
Figure 12B:
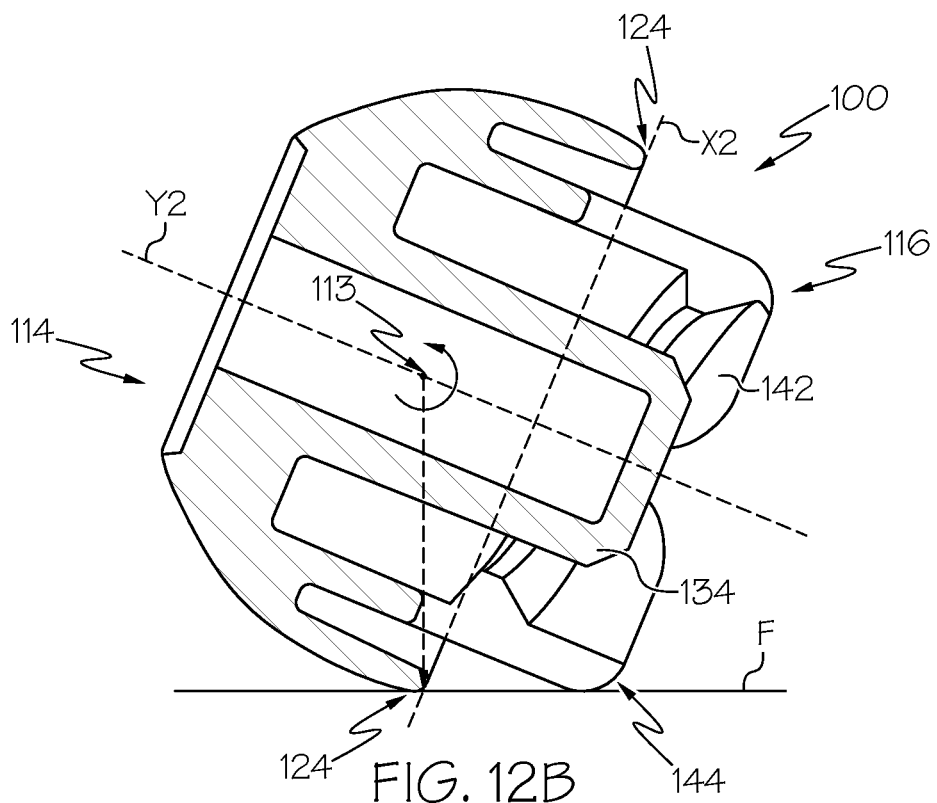
Figure 13:
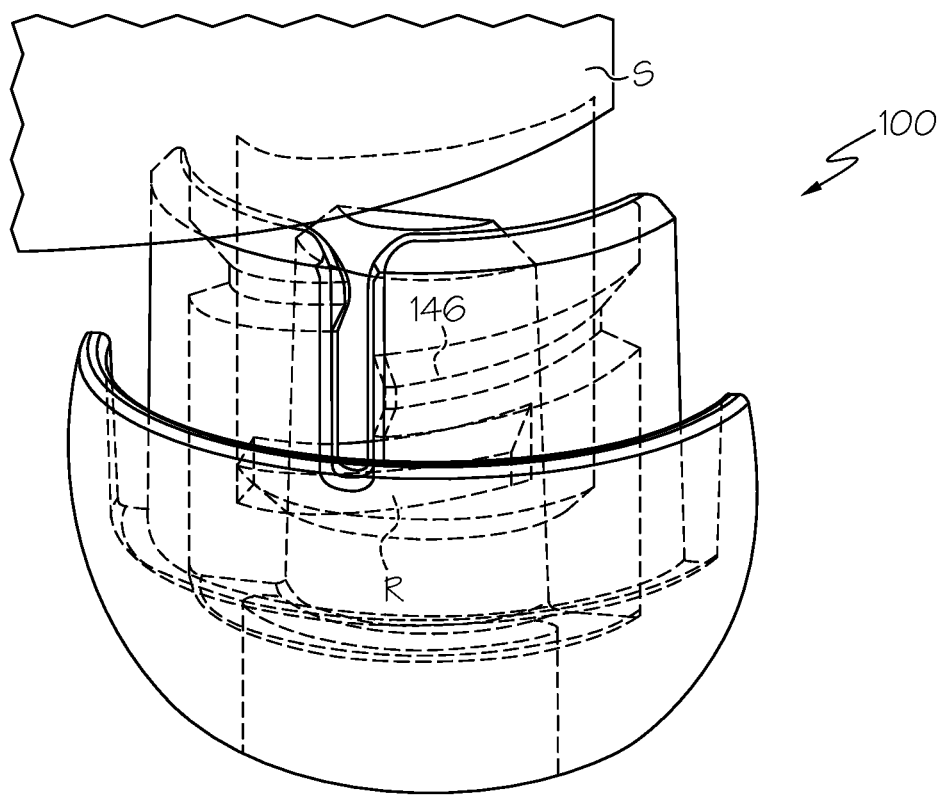
FIG. 13 shows a rear perspective view of a cross-sectional view of the self-righting tip cap of FIGS. 12A-B removably coupled to a syringe, and showing the interengagement of the rib of the female coupling of the syringe engaged with the threads of the cap.

Optionally, the extension or length of the coupling 134 may be sized as desired. For example, as shown in FIGS. 9-11, the extension of the coupling 134 is relatively small compared to the extension of the coupling 134 as shown in FIGS. 12-13. As shown in FIG. 11, when the coupling 134 is relatively short, the female coupling FC is capable of fitting entirely within the annular recess 136 (see the end of the female coupling FC contacting a bottom surface or floor of the annular recess 136). However, as depicted in FIGS. 12A-13, the length of the coupling 134 is substantially greater than the length of the coupling 134 of FIGS. 9-11, which may prevent the female coupling FC from fully engaging the coupling, for example, wherein the end of the female coupling FC is fully seated and in contact with the floor of the annular recess 136. Thus, for example, as depicted in FIG. 13, with the ribs R of the female coupling of the syringe S engaged with the threads 146 of the cap 100, the cap 100 becomes fully engaged with the female coupling FC and the end of the female coupling FC is generally laterally offset from the floor of the annular recess 136 when fully seated therewith. Optionally, the coupling 134 of FIGS. 12A-B may be sized accordingly such that the female coupling FC fits entirely within the annular recess 136, regardless of its length or extension. Preferably, the size and shape of the coupling 134 and the thread pitch can be adjusted accordingly, for example, to provide for the tip cap 100 removably coupling with the female coupling FC as desired. Optionally, according to additional example embodiments of the present invention, the coupling 134 may be sized and shaped as desired, for example, for coupling with other connectors, fittings, LUER connectors, etc.

FIGS. 12A-B show the center of gravity 113 of the tip cap 100. Preferably, the center of gravity 113 is positioned such that the tip cap preferably rights itself to a coupling orientation (with the edge 121 in contact with the flat surface F) to provide for receiving the female coupling FC. As shown in FIG. 12B, the center of gravity 113 of the cap 100 is substantially aligned or positioned above the rim 124 such that when the cap 100 is resting on the flat surface F (with the rim 124 and end portion 144 contacting the surface F), the cap 100 will roll and right itself wherein the base surface 120 is in contact with the flat surface F. For example, a generally vertical arrow is shown extending from the center of mass 113, which generally intersects with a tipping point plane X2 that is generally positioned adjacent the rim 124 thereof (and generally perpendicular relative to the elongate axis Y2), and wherein the vertical arrow and tipping point plane X2 generally intersect where the rim 124 is generally in contact with the surface F. Thus, according to some example forms, the center of mass 113 is positioned along the elongate axis Y2 and at a length C from the tipping point plane X2, and wherein the center of mass 113 is generally positioned directly atop (and at a distance therefrom) the intersection of the tipping point plane X2 and the rim 124. As depicted in FIG. 12A, the rim 124 defines a width A, the edge 121 defines a width B, the couplings 142 define a width D, and the center of gravity 113 is generally positioned at a length C from the tipping point plane X2, for example, in a direction towards the first end 114. Generally, the width A is greater than the width B, more preferably the width A is between about 1.15-1.50 times greater than the width B. According to some example forms, width A is greater than the width B, the width D, and the length C. According to other example forms, width D is between about 1.1-1.4 times larger than the width B, and the width A is between about 1.1-1.5 times larger than the width D. Optionally, the widths A, B, D and the length C may be sized as desired. Preferably, the extension of the portions thereof (coupling 134, body 112, rim 124, couplings 142, etc.), which are generally along the elongate axis Y2, may be sized as desired. Furthermore, the generally oblate spheroid external geometry or bulbous-shaped cap body 112 generally defines a curved side wall 118 (see FIG. 12A), which generally extends continuously between the edge 121 and the rim 124. According to some example forms, the curved side wall 118 is generally comprises a constant radius. Optionally, the wall 118 can comprise two or more radiuses as desired.

Figure 14:
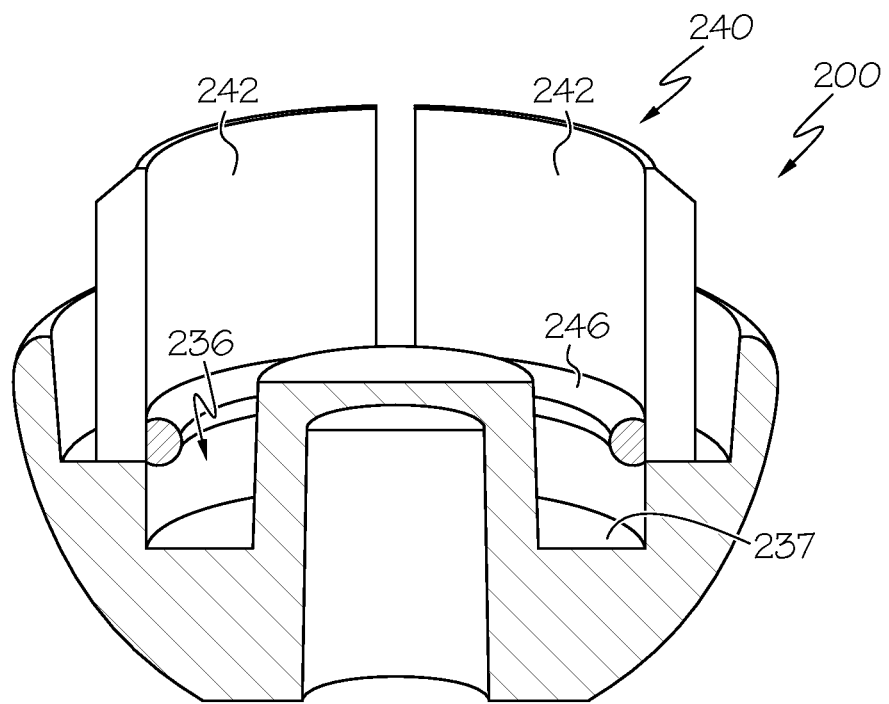
FIG. 14 shows a self-righting tip cap according to another example embodiment of the present invention.
Figure 15:
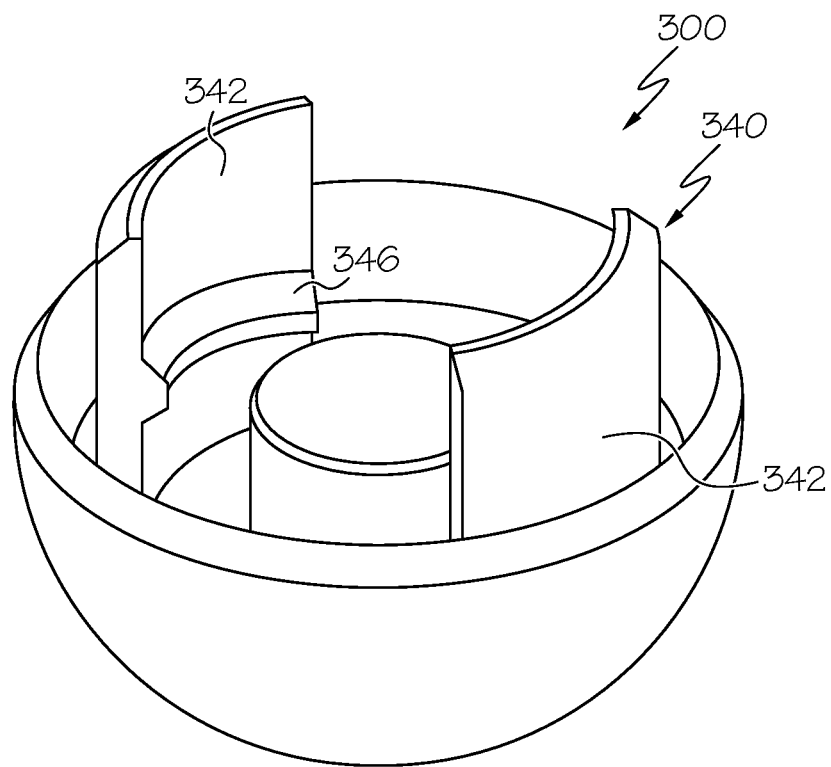
FIG. 15 shows a self-righting tip cap according to another example embodiment of the present invention.

FIGS. 14-15 show self-righting tip caps 200, 300 according to additional example embodiments of the present invention. As depicted in FIG. 14, the clips 242 preferably comprise a ridge or rim-like indent 246 protruding from at least a portion of the interior surfaces thereof at a generally equal height and generally spaced a distance away from a floor 237 of the annular recess 236. As such, when the female coupling FC is generally fully inserted or at least inserted within a portion of the receiving end of the tip cap 200, the ribs R of the coupling engage the indents 246 causing outward flexing of the clips 242 until the ribs R move beyond the indents 246, thereby allowing the clips 242 to return to a neutral state. As such, to remove the cap 200 from the female coupling FC of the syringe S, the cap is pulled away from the female coupling FC, for example, wherein the user grasps the cap 200 and pulls away from the syringe and/or female coupling FC. Preferably, the resiliency or flexibility of the clips 242 can be adjusted such that a particular pull-off force is required to remove the cap 200 from the female coupling FC. According to some example forms, a pull-off force of between about 1-8 pounds must be applied to the cap 200 for removal therefrom. Optionally, other forces less or greater than 1-8 pounds can be configured to allow for removal of the cap 200 from the female coupling FC.

As depicted in FIG. 15, the self-righting tip cap 300 comprises a pair of opposed clips 342, which are generally on opposite sides of the coupling 334. According to one form, at least a portion of the interior surfaces of the female coupling FC thereof comprises a thread protruding therefrom for interengagement with the ribs R of the female connector FC. Similarly to the cap 100, the cap 300 is rotated relative to the female coupling FC for removal therefrom. Optionally, the resiliency or flexibility of the clips 342 may be configured to provide for removal therefrom by pulling or a generally liner non-rotational force. Optionally, a combination of both rotational and linear may be utilized for removal.

Figure 16:
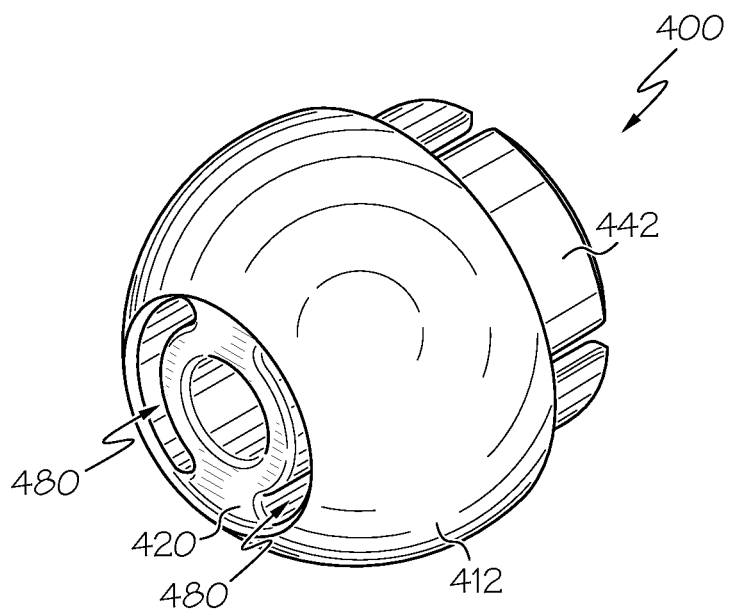
FIGS. 16 and 17A-B show a self-righting tip cap according to another example embodiment of the present invention, showing one or more openings formed therein.
Figure 17A:
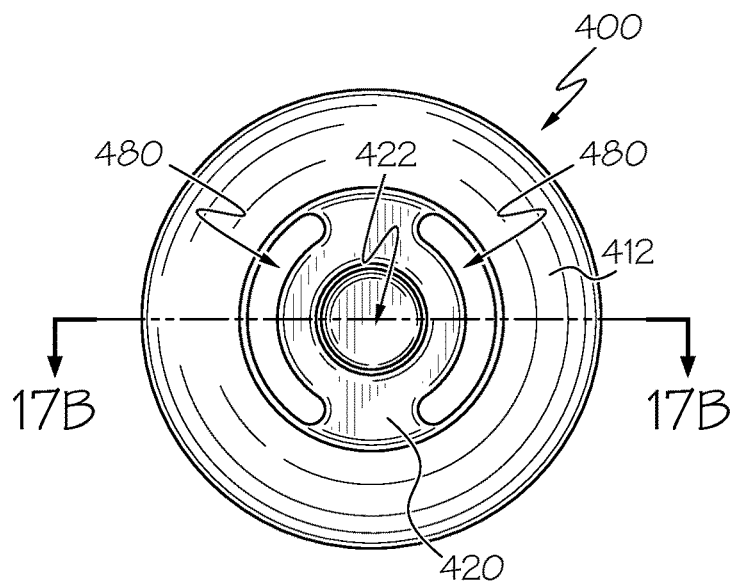
Figure 17B:
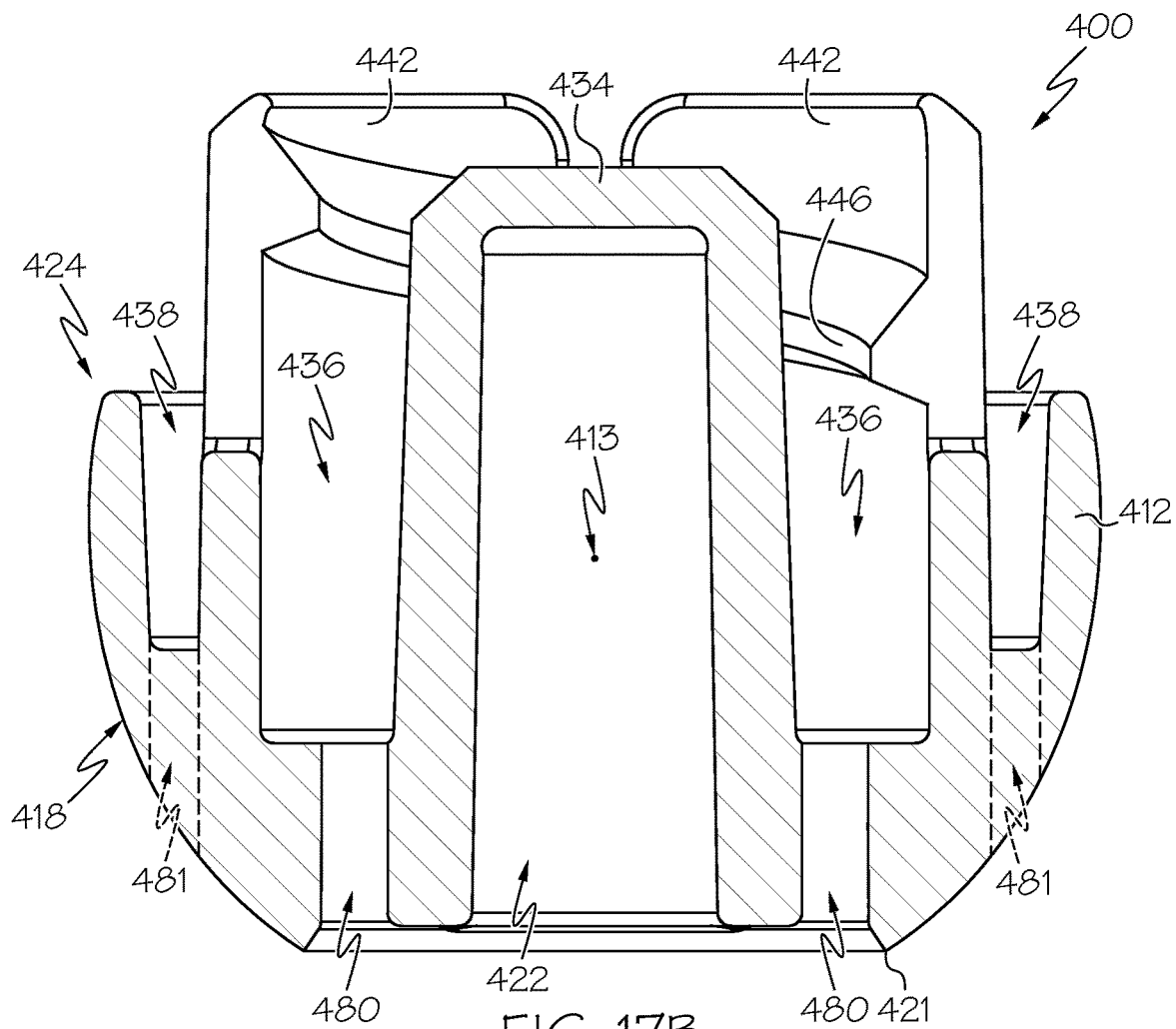
Figure 23:
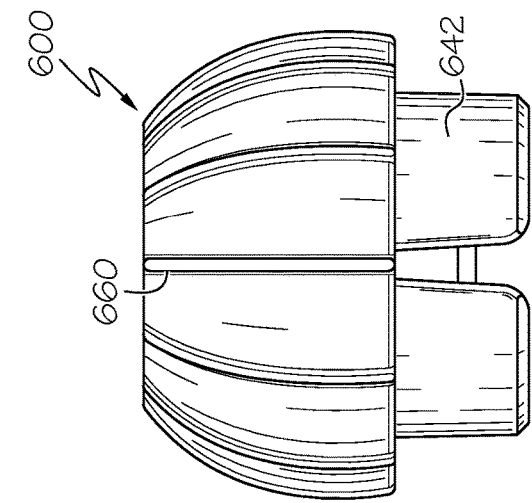
FIGS. 22-25 show several views of a self-righting tip cap according to another example embodiment of the present invention.
Figure 22:
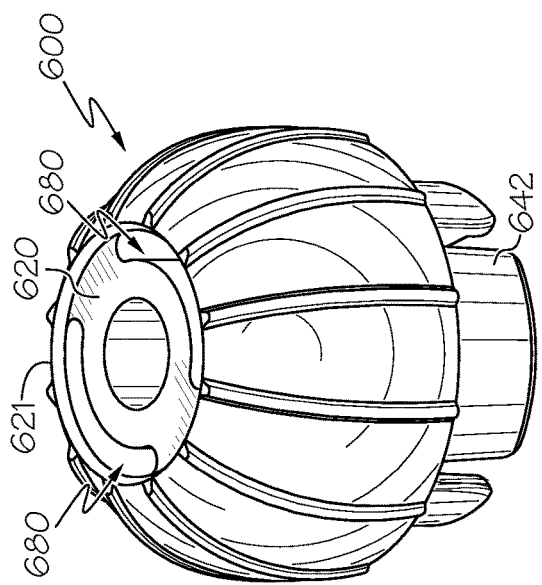
Figure 25:
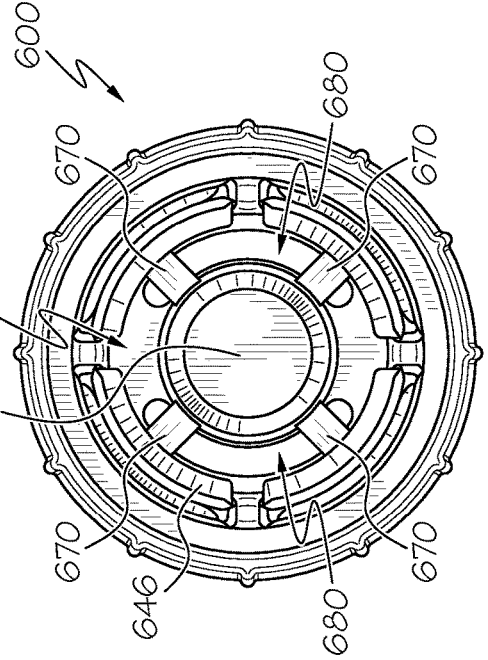
Figure 24:
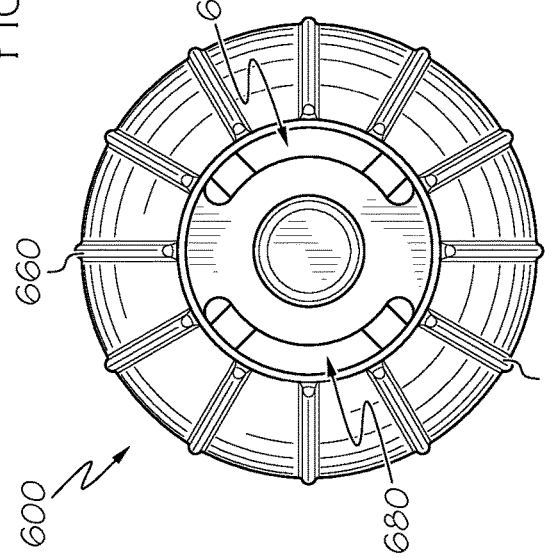
Figure 27:
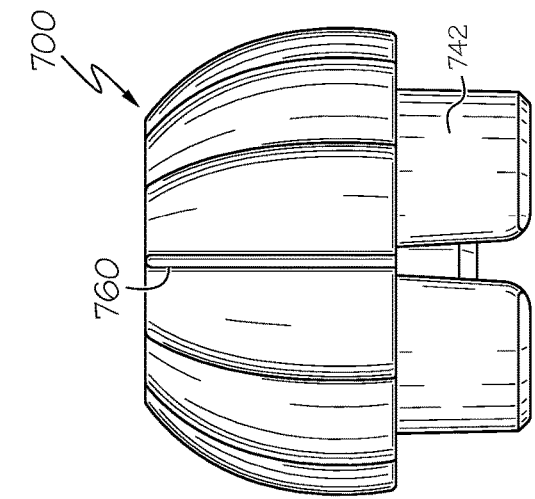
FIGS. 26-29 show several views of a self-righting tip cap according to another example embodiment of the present invention.
Figure 26:
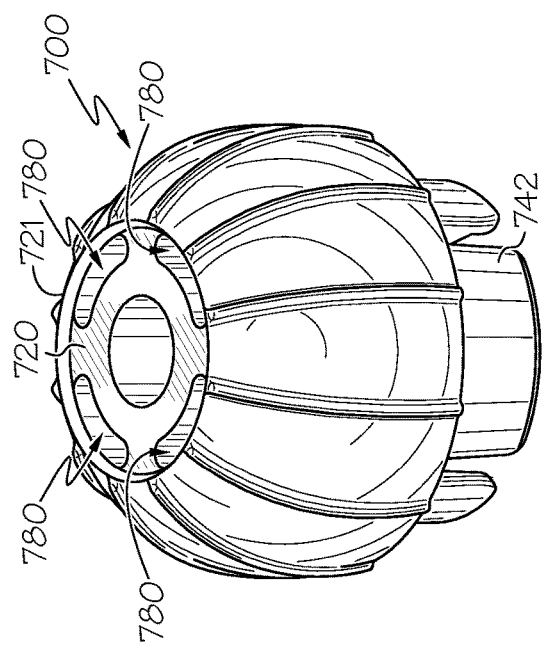
Figure 29:
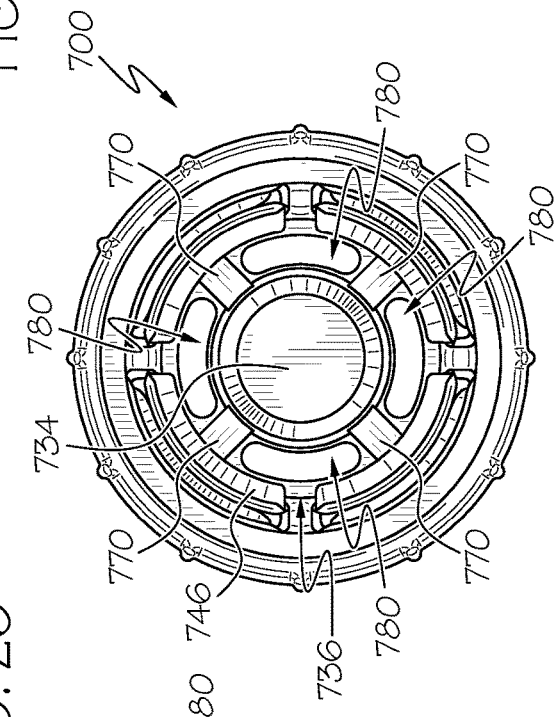
Figure 28:
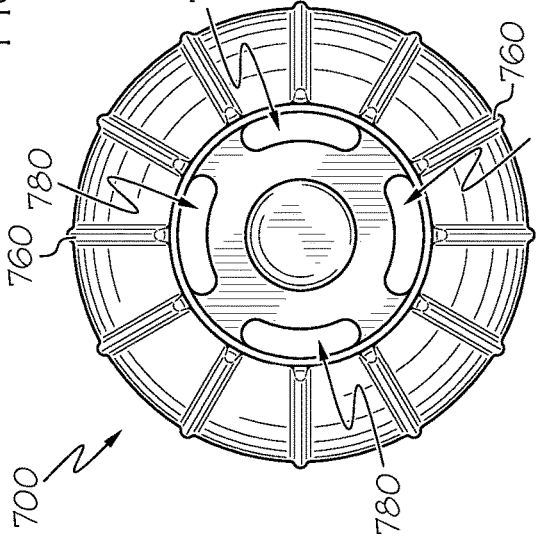

FIGS. 16 and 17A-B show a self-righting tip cap 400 according to another example form of the present invention. As depicted, the tip cap 400 preferably comprises one or more openings 480 extending through a portion thereof to mitigate potential choking hazards, and/or to provide drainage and venting of any fluid accumulation within the tip cap 400. In the depicted embodiment, two generally semi-circular openings 480 are formed within the base surface 420 of the cap 400 and extend to within the annular recess 436 that is defined between the coupling 434 and the clips 442 (see FIG. 17B). Optionally, one or three or more openings may be provided within the base surface or along other portions of the cap as desired. In example forms, the openings 480 do not communicate with the central orifice 422 that is formed within the coupling 434. And as described above with respect to the tip cap 10, the orifice 422 is formed within the coupling 434, but does not extend entirely therethrough, for example, since it is the coupling 434 which provides for sealing engagement with the female coupling FC of the syringe S. According to some example forms, a second annular recess 438 is formed between the clips 442 and a portion of the body 412 (generally near the second end 416). As such, one or more additional openings 481 may be provided for providing drainage of fluid that may accumulate within the second annular recess 438 (see dashed lines leading from bottom of second annular recess 438 to outer surface of body 412). Preferably, as depicted in FIG. 17B, the outer curved side wall 418 extends contiguously between the edge 121 and the rim 424. According to preferred forms, the center of mass 413 is generally positioned between the tipping point plane X2 (see FIGS. 12A-B) and the first end defined by the edge 421.

FIGS. 18-29 show additional example embodiments of a tip cap according to additional example embodiments of the present invention. FIGS. 18-21 show a tip cap 500. Generally, the tip cap 500 comprises the elements of the tip caps depicted above, which generally includes a body 512, clips 542 extending from a portion of the body 512, a coupling 534, a base surface 520, a curved side wall 518, and threads 546 formed on internal portions of the clips 542. As depicted, a radial array of rib-like indentions or nubs 560 extend along the curved outer surface of the body 512. In example forms, the nubs 560 preferably assist in a user gripping and/or twisting the tip cap 500, for example, for removing the tip cap 500 from engagement with the female coupling FC of the syringe S. Preferably, at least one tactile rib or support 570 is formed within the annular recess 536, which generally extends between the coupling 534 and the outer radial wall of the recess 536. In example forms, the tip cap 500 comprises four equally spaced supports 570 positioned about the annular recess. Generally, the supports 570 define four sections within the annular recess 536 whereby each of the supports 570 are generally centrally-positioned between their respective clip 542. According to some preferred forms, the supports 570 provide an amount of rigidity to the clips 542 such that they are generally flexible yet comprise a greater rigidity than the tip cap 100, which does not include supports 570. Optionally, the curved outer surface may comprise other surface features, indents, or other features to provide for assisting the user in gripping and/or twisting the cap. Optionally, the outer surface thereof is to be configured for interengagement with a machine, for example, whereby at least a portion of the capping process is automated or machine driven. Preferably, the center of mass 513 is generally positioned between the tipping point plane thereof (see FIGS. 12A-B) and the first end defined by edge 121.

FIGS. 22-25 show a tip cap 600 according to an additional example embodiment of the present invention. As depicted, the tip cap 600 is substantially similar to the tip cap 500 and comprises one or more openings 680 extending through a portion thereof to mitigate potential choking hazards, and/or to provide drainage and venting of any fluid accumulation within the tip cap. In the depicted embodiment, two generally semi-circular openings 680 are formed within the base surface 620 of the cap 600 and extend to within the annular recess 636 that is defined between the coupling 634 and the clips 642 (see FIG. 25). Generally, the openings 680 are positioned such that they generally occupy about two of the four sections defined by the supports 670, and whereby ends of the openings 680 are positioned within the other two sections of the four sections defined by the supports 670. Optionally, one or three or more openings 680 may be provided within the base surface 620 or along other portions of the cap 600 as desired. As depicted in FIGS. 26-29, a tip cap 700, which is substantially similar to the tip caps 500, 600, comprises four openings 780 formed through the base surface 720. Typically, each opening 780 is generally positioned within each of the four sections defined by the supports 670. Optionally, the openings 780 may be generally offset relative to the sections such that each opening 780 extends between two of the four sections.

FIGS. 30-31 show a tip cap 800 according to another example embodiment of the present invention. As depicted, the tip cap 800 is substantially similar to the tip caps 500, 600, 700 as described above. Preferably, a substantially cylindrical recess or orifice 890 is formed within the coupling 834, but does not extend through the entire tip cap 800. According to some example forms, a lumen extension tip L is formed within the female coupling FC and communicates with the internal area of the syringe body. Thus, to provide for interengagement of the female coupling FC including the lumen extension tip L, the orifice 890 provides a cavity or pocket for receiving the lumen extension tip L of the female coupling FC. Typically, the lumen extension tip L is substantially centrally and axially positioned relative to a generally elongate axis of the syringe S. Optionally, as described above, the tip cap 800 can comprise one or more openings formed within the base surface of the cap.

Figure 32:
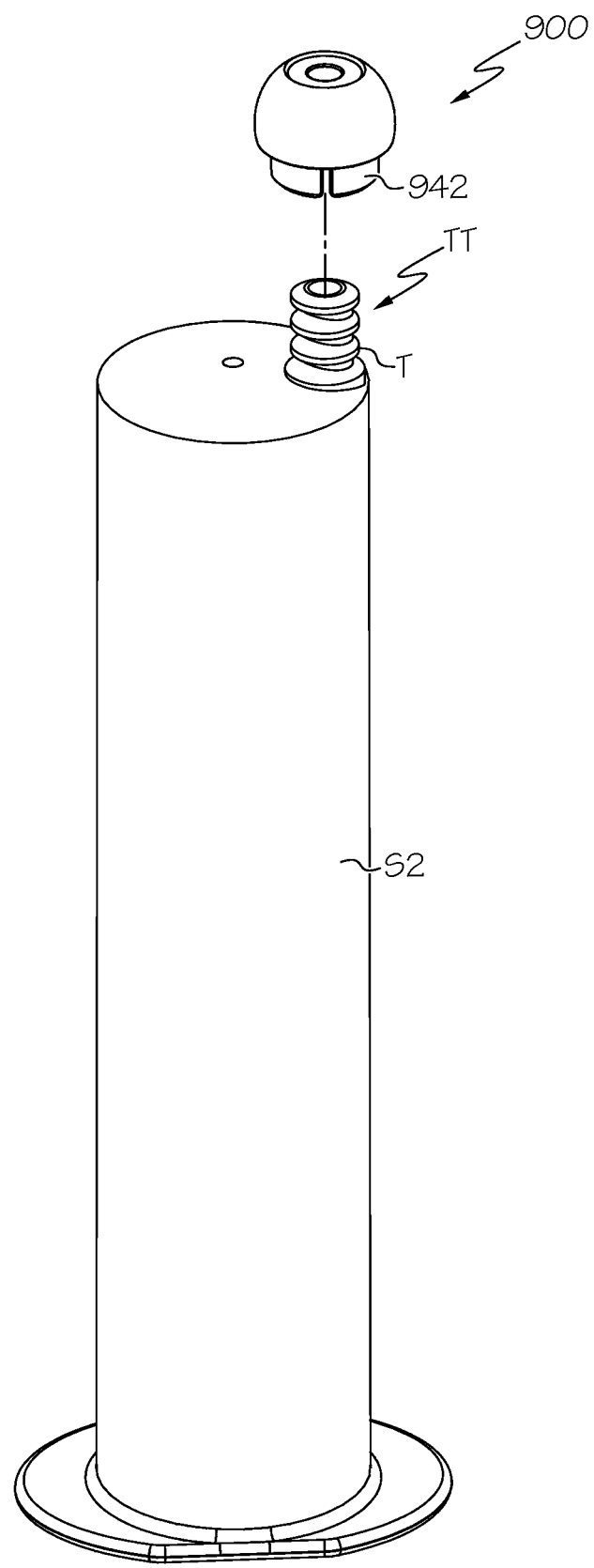
FIGS. 32-34 show a self-righting tip cap mounted to a syringe having a threaded syringe tip according to another example embodiment of the present invention.

FIG. 32 shows a syringe S2 having threaded syringe tip, for example, to which example embodiments of a self-righting tip cap can be applied within the scope of the present invention. Generally, the syringe S2 comprises a threaded female connector or tip TT comprising threads T, which is configured for interengagement of a self-righting tip cap 900 (substantially as described above) thereon. In example forms, the threaded tip TT comprises threads positioned along a helical path around the entire portion of the tip of the syringe, rather than lugs or ribs R extending along a portion of the periphery of the tip of a syringe S as described above (see FIG. 2).

Figure 33:
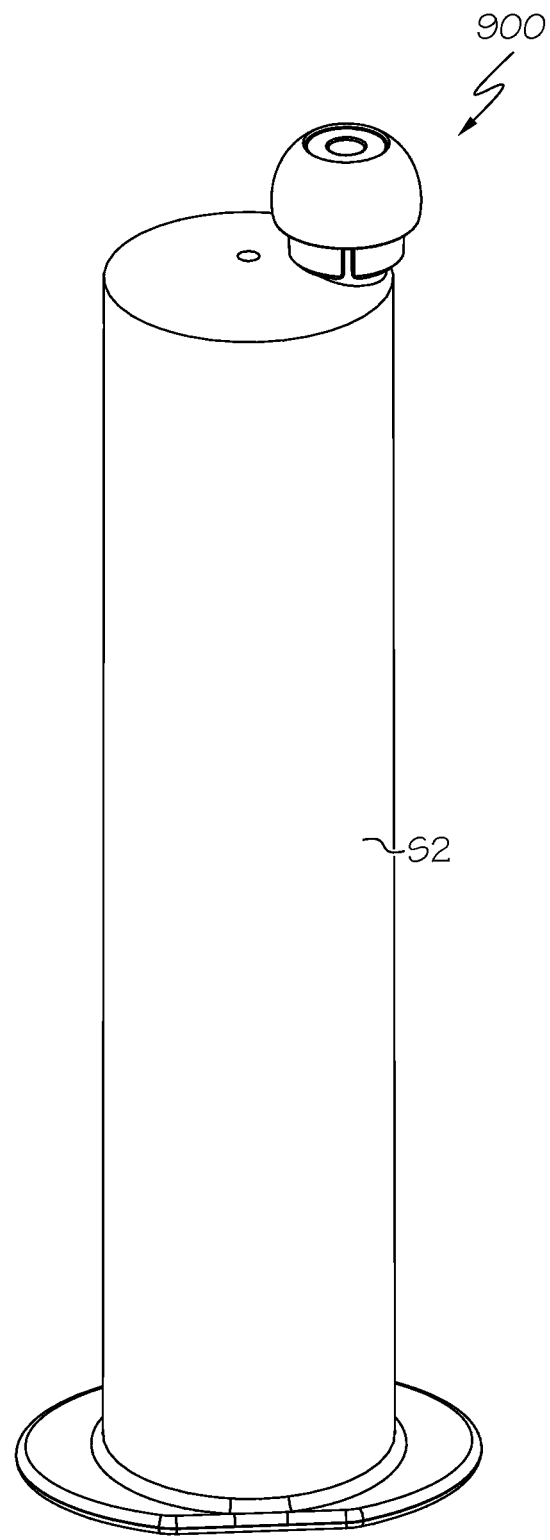
Figure 34:
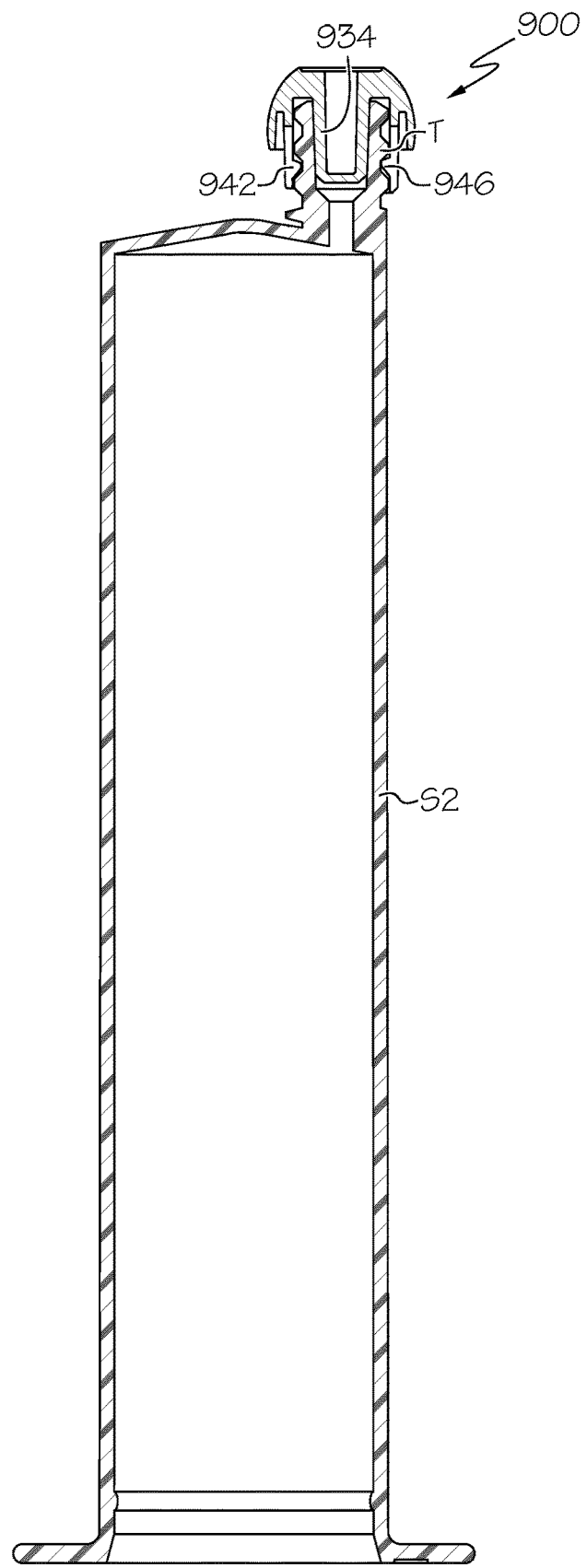

According to some example forms, the syringe S2 can include a threaded tip TT that is integrally formed with the syringe S2. Optionally, the tip may generally be free from threads and a generally cylindrical or tubular collar member with threads on an exterior portion thereof can be permanently (or removably) mounted to the unthreaded tip. As depicted in FIGS. 32-34, the tip cap 900 can be mounted to the threaded tip TT by pressing and/or screwing the tip cap onto the syringe tip. For example, according to one example form, the tip cap 900 can be generally snapped on to the threaded tip TT wherein the clips 942 generally flex outwardly such that the threads 946 thereof ride over the threads T until properly seating on the threaded tip TT. Additional rotation of the tip cap 900 relative to the threaded tip may be provided for further seating of the tip cap 900 with the threaded tip TT. Optionally, the tip cap 900 can be rotationally screwed onto the threaded tip TT, for example, wherein the tip cap 900 from the initial engagement therebetween is rotated such that the threads 946 interengage the threads T of the threaded tip TT, and wherein further rotation is provided until the tip cap 900 is fully seated with the threaded tip TT (see FIGS. 33-34).

For removing the tip cap 900 from the threaded tip TT, the tip cap 900 is generally rotated until becoming disengaged therefrom. Optionally, the clips 942 may also be configured such that a user can grasp the tip cap 900 and pull directly off, for example, whereby the clips 942 flex outwardly to disengage the threads 946 from the threads T of the threaded tip TT. Optionally, other tip caps as described herein may be configured for removable engagement with the threaded tip TT of the syringe S2. The syringe tip TT can be configured as an ENFit or ISO 80369 compatible female connector modified with continuous external threading as shown, or alternatively can comprise other female or male tip configurations; and the coupling features of the tip cap 900 can be adapted to correspond to the particular syringe tip configuration while maintaining the tip cap's self-righting characteristics.

FIGS. 35A-E show further details of the threaded tip TT according to example embodiments of the present invention. As described above, the threaded tip TT can be integrally formed with the syringe or the threaded tip may be a separate coupling for removably or permanently coupling to the syringe. According to example forms, the nominal length AA of the threaded tip TT is between about 5.56 mm to about 12.98 mm, more preferably about 9.27 mm, the pitch BB of the threads T is between about 1.47 mm to about 3.43 mm, more preferably about 2.45 mm, the outer diameter CC of the threaded portion is between about 4.01 mm to about 9.35 mm, more preferably about 6.68 mm, the diameter DD of the lumen that is generally centrally-positioned within the threaded tip TT is between about 0.95 mm to about 2.23 mm, more preferably about 1.59 mm, the crest width EE of the threads T is between about 0.71 mm to about 1.65 mm, more preferably about 1.18 mm, and the height FF of the threads T generally measured between the root and crest is between about 0.39 mm to about 0.90 mm, more preferably about 0.64 mm. Preferably, one or more of the dimensions depicted may be adjusted as desired, for example, by between about ±1-35%, or may be otherwise sized as desired.

Figure 36:
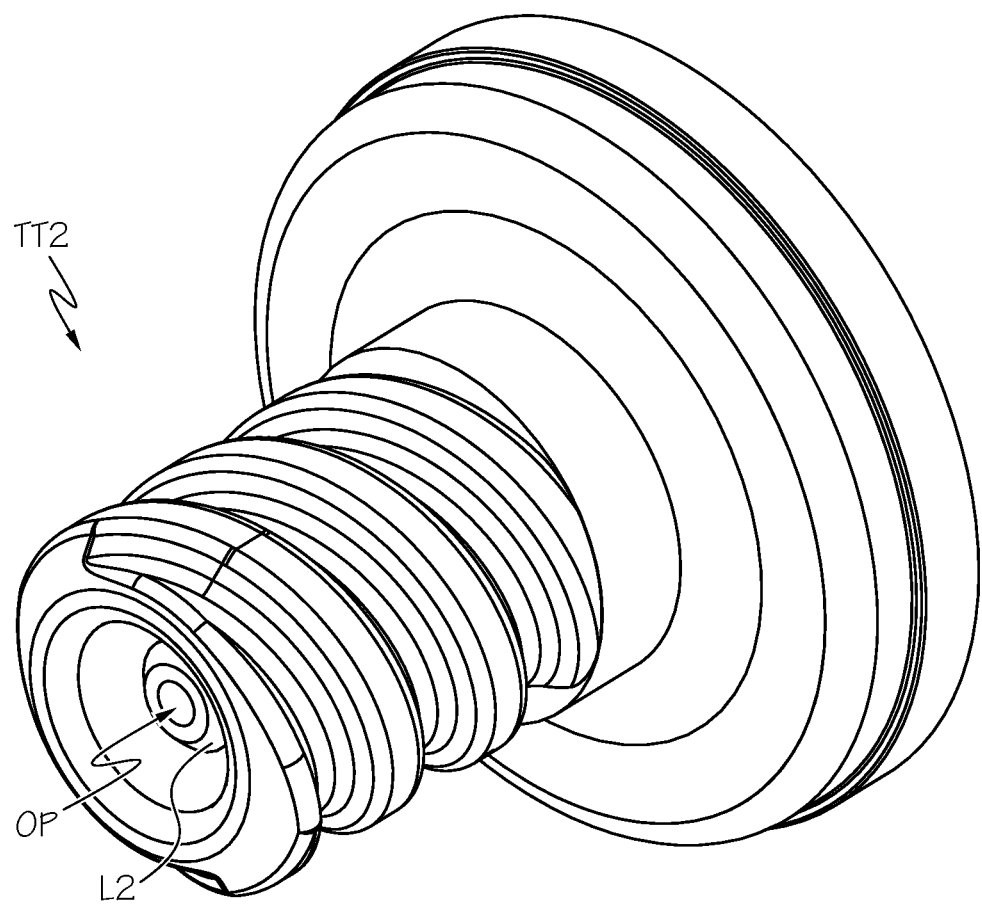
FIG. 36 shows a threaded syringe tip according to another example embodiment of the present invention.

FIG. 36 shows a threaded tip TT according to another example embodiment of the present invention. As depicted, the threaded tip TT2 is substantially similar to the threaded tip TT as described above. Preferably, a lumen extension tip L2 is provided with the threaded tip TT2, which is generally centrally-positioned and axially extending within a portion thereof, and which comprises a lumen or opening OP extending therethrough for allowing fluid to pass therethrough. According to example forms, the lumen extension tip L2 preferably reduces the volume of fluid within the threaded tip TT2, for example, when the threaded tip TT2 is coupled to a coupling or other fluid connector. Thus, by providing the lumen extension tip L2, dosing inaccuracies are substantially reduced if not entirely eliminated. Accordingly, as similarly depicted with respect to FIGS. 30-31, the tip cap 900 can comprise an orifice within the coupling 934 (see FIG. 34) for receiving the lumen extension tip L2.

While the invention has been described with reference to preferred and example embodiments, it will be understood by those skilled in the art that a variety of modifications, additions and deletions are within the scope of the invention, as defined by the following claims.

What is claimed is:

1. A self-righting tip cap comprising:
a cap body comprising a generally oblate spheroid external geometry with a first end and a second end at opposite sides of the cap body;
a base surface at the first end defining a generally planar rim surrounding the base surface;
a coupling element accessible from the second end, the coupling element providing for removable engagement with a connector of a syringe; and
at least one clip extending from an inner portion of the cap body towards the second end, an interior face thereof comprising an indent protruding therefrom, the at least one clip being configured to provide for a non-rotational snap fit coupling engagement with the connector of the syringe,
wherein the coupling element is sealingly engagable with the connector of the syringe without any rotation of the cap body, the at least one clip being at least partially flexible so as to allow for at least some temporary displacement thereof during axial, non-rotational attachment of the coupling element with the connector of the syringe.

2. The self-righting tip cap of claim 1, wherein the indent protruding from the at least one clip is in the form of a thread.

3. The self-righting tip cap of claim 2, wherein the at least one clip is generally resiliently flexible.

4. The self-righting tip cap of claim 1, further comprising an annular recess surrounding the coupling element.

5. The self-righting tip cap of claim 4, further comprising at least one opening formed within the base surface and communicating with the annular recess.

6. The self-righting tip cap of claim 4, further comprising at least one rib or support positioned within the annular recess and extending between an interior portion of the at least one clip and the coupling element.

7. The self-righting tip cap of claim 1, further comprising grooves or indents extending along an outer surface of the cap body.

8. The self-righting tip cap of claim 7, wherein the grooves or indents are generally positioned in a radial array about the outer surface of the cap body.

9. The self-righting tip cap of claim 1, wherein the coupling element comprises an orifice formed therein for receiving a lumen extension tip of a connector of a syringe.

10. The self-righting tip cap of claim 1, wherein the cap body defines a rim formed along an outer portion thereof near the second end, wherein the end of the at least one clip defines an end portion, and wherein with the self-righting tip cap in contact with a surface so that both the rim and the end portion are in contact with the surface, the self-righting tip cap will right itself to a coupling-side-up orientation.

11. The self-righting tip cap of claim 10, wherein the rim of the cap body defines a tipping point plane, wherein the center of mass is positioned along an axis that is generally perpendicular with the tipping point plane and between the tipping point plane and the first end thereof.

12. The self-righting tip cap of claim 1, wherein the at least one clip can optionally provide for rotational coupling engagement with the connector of the syringe.

13. A syringe and tip cap assembly comprising:
a syringe comprising a connector; and
a self-righting tip cap configured for removable attachment to the connector of the syringe, the self-righting tip cap comprising:
a cap body comprising a generally oblate spheroid external geometry with a first end and a second end at opposite sides of the cap body;
a base surface at the first end defining a generally planar rim surrounding the base surface;
a coupling element accessible from the second end, the coupling element providing for removable engagement with the connector of the syringe; and
a split collar extending from an inner portion of the cap body towards the second end, the split collar comprising a circular array of clips such that the coupling element can be coupled with the connector by axial, non-rotational engagement.

14. The syringe and tip cap assembly of claim 13, further comprising a thread portion protruding from an interior portion of at least one clip of the circular array of clips.

15. The syringe and tip cap assembly of claim 14, further comprising a rib portion formed on the connector of the syringe, and wherein the thread portion of the at least one clip provides for removable engagement with the rib portion of the connector.

16. The syringe and tip cap assembly of claim 13, wherein at least one clip of the circular array of clips is generally resiliently flexible.

17. The syringe and tip cap assembly of claim 13, further comprising an annular recess surrounding the coupling element.

18. The syringe and tip cap assembly of claim 17, further comprising at least one opening formed within the base surface and communicating with the annular recess.

19. The self-righting tip cap of claim 17, further comprising at least one rib or support positioned within the annular recess and extending between an interior portion of the at least one clip and the coupling element.

20. The syringe and tip cap assembly of claim 13, further comprising grooves or indents extending along an outer surface of the cap body.

21. The syringe and tip cap assembly of claim 20, wherein the grooves or indents are generally positioned in a radial array about the outer surface of the cap body.

22. The syringe and tip cap assembly of claim 13, wherein the coupling element comprises an orifice formed therein for receiving a lumen extension tip of the connector of the syringe.

23. The syringe and tip cap assembly of claim 13, wherein the split collar can optionally provide for rotational coupling engagement with the connector of the syringe.

24. A self-righting tip cap comprising:
a cap body comprising a generally oblate spheroid external geometry with a first end and a second end at opposite sides of a minor axis of the cap body;
a base surface at the first end defining a generally planar contact surface;
an irregular surface at the second end; and
a coupling element accessible from the second end but not extending beyond the second end, wherein the irregular surface at the second end comprises alternating peaks and valleys, and wherein the coupling element generally extends beyond the valleys but not beyond the peaks of the irregular surface at the second end of the cap body.

25. The self-righting tip cap of claim 24, wherein the opposing peaks and valleys comprise a wave-like profile.

26. The self-righting tip cap of claim 25, wherein the wave-like profile comprises smooth and radiused transitions between the peaks and the valleys.

27. The self-righting tip cap of claim 24, wherein the coupling element provides for removable engagement with a connector of a syringe.

28. The self-righting tip cap of claim 24, further comprising grooves along an outer surface of the cap body.

29. The self-righting tip cap of claim 24, further comprising an annular recess surrounding the coupling element.

30. A syringe and tip cap assembly comprising:
a syringe comprising a threaded tip having substantially continuous external threads extending along at least a portion thereof, the substantially continuous external threads extending along a helical path; and
a self-righting tip cap configured for removable attachment to the threaded tip of the syringe, the self-righting tip cap comprising:
a cap body comprising a generally oblate spheroid external geometry with a first end and a second end at opposite sides of the cap body;
a base surface at the first end defining a generally planar contact surface;
at least one coupling element compatible with the substantially continuous external threads of the threaded tip of the syringe; and
a clipped collar generally surrounding the at least one coupling element and extending towards the second end, the clipped collar comprising at least one clip comprising at least a portion of a thread protruding from an inner surface thereof,
wherein the self-righting tip cap can be mounted to the threaded tip by pressing and/or screwing the tip cap on the threaded tip, wherein the self-righting tip cap can be pressed on the threaded tip such that the thread portion of the at least one clip rides over the threads of the threaded tip, causing the at least one clip to flex outwardly, until the at least one coupling element seats with the threaded tip, and wherein the self-righting tip cap can be screwed on the threaded tip such that the thread of the at least one clip threadingly engages with the threaded tip until the at least one coupling element seats with the threaded tip.

31. The syringe and tip cap assembly of claim 30, wherein the at least one coupling element of the tip cap is positioned at the second end of the cap body, generally opposite the base surface, the at least one coupling element comprising a generally central coupling and an annular recess formed around the coupling, and wherein an outer wall of the annular recess comprises threads protruding therefrom for removable engagement with the threaded tip of the syringe.

32. The syringe and tip cap assembly of claim 31, further comprising a lumen extension tip formed within the threaded tip of the syringe, and wherein the coupling comprises an orifice for receiving the lumen extension tip.

* * * * *